US011292993B2

(12) United States Patent
Brezoczky et al.

(10) Patent No.: US 11,292,993 B2
(45) Date of Patent: Apr. 5, 2022

(54) SYSTEMS AND PROCESSES FOR TREATING TEXTILES WITH AN ANTIMICROBIAL AGENT

(71) Applicant: Applied Silver, Inc., Hayward, CA (US)

(72) Inventors: Thomas Brezoczky, Los Gatos, CA (US); Sean Morham, San Francisco, CA (US); William Morris, San Francisco, CA (US); David Brown, Danville, CA (US); Keith Copenhagen, Oakland, CA (US)

(73) Assignee: Applied Silver, Inc., Hayward, CA (US)

( * ) Notice: Subject to any disclaimer, the term of this patent is extended or adjusted under 35 U.S.C. 154(b) by 0 days.

(21) Appl. No.: 16/458,997

(22) Filed: Jul. 1, 2019

(65) Prior Publication Data
US 2020/0109356 A1 Apr. 9, 2020

Related U.S. Application Data

(60) Continuation of application No. 15/870,944, filed on Jan. 13, 2018, now Pat. No. 10,351,807, which is a division of application No. 15/085,539, filed on Mar. 30, 2016, now abandoned.

(60) Provisional application No. 62/297,304, filed on Feb. 19, 2016, provisional application No. 62/208,444, filed on Aug. 21, 2015.

(51) Int. Cl.
*C11D 3/48* (2006.01)
*D06F 35/00* (2006.01)
*A61L 2/18* (2006.01)
*C11D 11/00* (2006.01)
*D06M 16/00* (2006.01)
*C11D 7/10* (2006.01)
*D06F 31/00* (2006.01)
*C02F 103/02* (2006.01)

(52) U.S. Cl.
CPC .......... *C11D 3/48* (2013.01); *A61L 2/18* (2013.01); *C11D 7/10* (2013.01); *C11D 11/0017* (2013.01); *C11D 11/0064* (2013.01); *D06F 35/006* (2013.01); *D06M 16/00* (2013.01); *C02F 2103/02* (2013.01); *D06F 31/005* (2013.01); *D10B 2509/00* (2013.01)

(58) Field of Classification Search
CPC .... C02F 1/505; C02F 2103/02; D06F 35/006; D06F 35/008; D06F 38/028; D06F 38/004; D06F 38/083; D06F 39/028; D06F 39/083; D06F 34/22; D06F 31/005; A61L 2/18; C11D 3/48; C11D 11/0017; C11D 11/0064; D06M 16/00; D10B 2509/00
See application file for complete search history.

(56) References Cited

U.S. PATENT DOCUMENTS

| | | | |
|---|---|---|---|
| 3,751,885 A | 8/1973 | McNeely | |
| 4,048,032 A | 9/1977 | Eibl | |
| 4,098,660 A | 7/1978 | Eibl et al. | |
| 4,119,518 A | 10/1978 | Miller | |
| 4,145,291 A | 3/1979 | Console et al. | |
| 4,198,296 A | 4/1980 | Doumas et al. | |
| 4,525,253 A | 6/1985 | Hayes et al. | |
| 4,545,956 A | 10/1985 | Ciszewski et al. | |
| 4,696,742 A | 9/1987 | Shimazaki | |
| 4,710,282 A | 12/1987 | Chak et al. | |
| 4,755,268 A | 7/1988 | Matsuo et al. | |
| 4,933,870 A | 6/1990 | Chang | |
| 4,995,975 A | 2/1991 | Jacquot et al. | |
| 5,190,659 A | 3/1993 | Wang et al. | |
| 5,281,312 A | 1/1994 | Woodside | |
| 5,342,528 A | 8/1994 | Adachi et al. | |
| 5,364,512 A | 11/1994 | Earl | |
| 5,632,904 A | 5/1997 | Samad et al. | |

(Continued)

FOREIGN PATENT DOCUMENTS

| | | |
|---|---|---|
| CH | 698955 | 12/2009 |
| CN | 1218009 | 6/1999 |

(Continued)

OTHER PUBLICATIONS

International Search Report issued in International Application No. PCT/US2016/047367; ISA/US, dated Dec. 28, 2016, 6 pages.
Written Opinion issued in International Application No. PCT/US2016/047367, ISA/US, dated Dec. 28, 2016, 12 pages.
Liu et al., "Controlled Release of Biologically Active Silver from Nanosilver Surfaces," ACS Nano, 2010, pp. 6903-6913, vol. 4, No. 11.

(Continued)

*Primary Examiner* — Amina S Khan
(74) *Attorney, Agent, or Firm* — McDonnell Boehnen Hulbert & Berghoff LLP

(57) ABSTRACT

According to an aspect of the present disclosure, a method of treating a textile with an antimicrobial agent over a plurality of laundry cycles each including a wash cycle and a treatment cycle is described. The method includes (a) receiving a textile in a wash system for a first laundry cycle, (b) initiating a wash cycle comprising a detergent, (c) initiating a post-detergent treatment cycle comprising dosing the textile with a solution having a predetermined concentration of an antimicrobial agent that comprises a metallic ion, and (c) repeating steps (a)-(c) for each of a plurality of additional laundry cycles. The predetermined concentration is insufficient to achieve a predetermined antimicrobial efficacy for the textile due to the first laundry cycle alone but sufficient to achieve the predetermined antimicrobial efficacy for the textile due to a combination of the first laundry cycle and one or more of the plurality of additional laundry cycles.

23 Claims, 10 Drawing Sheets

(56) References Cited

U.S. PATENT DOCUMENTS

| | | | |
|---|---|---|---|
| 5,765,403 A | 6/1998 | Lincoln et al. | |
| 5,782,109 A | 7/1998 | Spriggs et al. | |
| 5,787,537 A | 8/1998 | Mannillo | |
| 5,843,284 A | 12/1998 | Waters et al. | |
| 5,858,246 A | 1/1999 | Rafter et al. | |
| 6,022,459 A | 2/2000 | Briggs et al. | |
| 6,128,931 A | 10/2000 | Woods | |
| 6,254,894 B1 | 7/2001 | Denkewicz, Jr. et al. | |
| 6,267,885 B1 | 7/2001 | Briggs et al. | |
| 6,303,039 B1 | 10/2001 | Back et al. | |
| 6,398,927 B1 | 6/2002 | Merzhauser | |
| 6,508,929 B1 | 1/2003 | Mercer | |
| 6,514,406 B1 | 2/2003 | Katehis | |
| 6,524,540 B1 | 2/2003 | Heinig, Jr. | |
| 6,562,243 B2 | 5/2003 | Sherman | |
| 6,634,048 B1 | 10/2003 | Hornung et al. | |
| 6,641,829 B1 | 11/2003 | Green et al. | |
| 6,761,827 B2 | 7/2004 | Coffey | |
| 6,838,095 B2 | 1/2005 | Newman et al. | |
| 6,929,740 B2 | 8/2005 | Hayes | |
| 6,982,039 B1 | 1/2006 | Butkus et al. | |
| 7,012,053 B1 | 3/2006 | Barnabus et al. | |
| 7,152,759 B2 | 12/2006 | Walton | |
| 7,322,065 B2 | 1/2008 | Kim et al. | |
| 7,384,564 B2 | 6/2008 | Bo | |
| 7,413,667 B1 | 8/2008 | Routberg et al. | |
| 7,422,759 B2 | 9/2008 | Kepner et al. | |
| 7,481,081 B2 | 1/2009 | Hsu et al. | |
| 7,487,876 B2 | 2/2009 | Maeda | |
| 7,540,966 B2 | 6/2009 | Costa et al. | |
| 7,550,746 B2 * | 6/2009 | Tokhtuev | G01N 21/6402 |
| | | | 250/461.1 |
| 7,597,718 B2 | 10/2009 | Yoshikawa et al. | |
| 7,617,704 B2 | 11/2009 | Iimori et al. | |
| 7,624,601 B2 | 12/2009 | Ikemizu et al. | |
| 7,708,896 B2 | 5/2010 | Ooe et al. | |
| 7,807,199 B2 | 10/2010 | Allen et al. | |
| 7,807,661 B2 | 10/2010 | Ylitalo et al. | |
| 7,819,127 B1 | 10/2010 | Huffman | |
| 7,882,647 B2 | 2/2011 | Ikemizu | |
| 7,934,402 B2 | 5/2011 | Lee | |
| 7,942,024 B2 | 5/2011 | Lee | |
| 7,950,254 B2 | 5/2011 | Gray et al. | |
| 7,972,519 B2 | 7/2011 | Koos et al. | |
| 8,002,898 B2 | 8/2011 | Schepers et al. | |
| 8,118,912 B2 | 2/2012 | Rodriguez et al. | |
| 8,173,067 B2 | 5/2012 | Eldred | |
| 8,239,990 B2 | 8/2012 | Lim et al. | |
| 8,309,506 B2 | 11/2012 | Sunder et al. | |
| 8,361,505 B1 | 1/2013 | Perry | |
| 8,394,420 B2 | 3/2013 | Kepner et al. | |
| 8,449,732 B2 | 5/2013 | Choi | |
| 8,460,395 B2 | 6/2013 | Smulowitz | |
| 8,563,447 B2 | 10/2013 | Canada | |
| 8,641,947 B2 | 2/2014 | Schmuhl et al. | |
| 8,729,008 B2 | 5/2014 | Begli et al. | |
| 9,132,296 B2 | 9/2015 | Wingfield | |
| 10,351,807 B2 * | 7/2019 | Brezoczky | D06F 39/028 |
| 2001/0049846 A1 * | 12/2001 | Guzzi | D06F 33/00 |
| | | | 8/158 |
| 2002/0189954 A1 | 12/2002 | Miyazaki et al. | |
| 2003/0170453 A1 | 9/2003 | Foss et al. | |
| 2003/0190370 A1 | 10/2003 | Kim et al. | |
| 2003/0196282 A1 | 10/2003 | Fyvie et al. | |
| 2003/0230122 A1 | 12/2003 | Lee | |
| 2004/0025263 A1 | 2/2004 | Kim et al. | |
| 2004/0031764 A1 | 2/2004 | Heinig, Jr. | |
| 2004/0205899 A1 | 10/2004 | Park et al. | |
| 2004/0214495 A1 | 10/2004 | Foss et al. | |
| 2005/0019568 A1 | 1/2005 | Foss et al. | |
| 2005/0037057 A1 | 2/2005 | Schuette et al. | |
| 2005/0095158 A1 | 5/2005 | Kirschner et al. | |
| 2005/0118281 A1 | 6/2005 | Newman et al. | |
| 2005/0155939 A1 | 7/2005 | Stadelmann | |
| 2005/0188731 A1 | 9/2005 | Aouad | |
| 2005/0194297 A1 | 9/2005 | Dorward | |
| 2005/0224419 A1 | 10/2005 | Wien et al. | |
| 2005/0226914 A1 * | 10/2005 | Cottrell | A01N 59/16 |
| | | | 424/443 |
| 2005/0229327 A1 | 10/2005 | Casella et al. | |
| 2006/0110258 A1 | 5/2006 | Iimura et al. | |
| 2006/0123562 A1 | 6/2006 | Ghosh et al. | |
| 2006/0127457 A1 | 6/2006 | Buchalter | |
| 2006/0130533 A1 | 6/2006 | Ooe et al. | |
| 2006/0164093 A1 | 7/2006 | Ooe | |
| 2006/0186222 A1 | 8/2006 | Ikemizu et al. | |
| 2006/0265814 A1 | 11/2006 | Ritter | |
| 2007/0004300 A1 | 1/2007 | Kreider et al. | |
| 2007/0044820 A1 | 3/2007 | Chan et al. | |
| 2007/0045176 A1 | 3/2007 | Chandra et al. | |
| 2007/0134301 A1 | 6/2007 | Ylitalo et al. | |
| 2007/0163097 A1 | 7/2007 | Metcalfe et al. | |
| 2007/0175833 A1 | 8/2007 | Ikeboh et al. | |
| 2007/0243380 A1 | 10/2007 | Vegad et al. | |
| 2007/0243781 A1 | 10/2007 | Chou | |
| 2007/0251022 A1 * | 11/2007 | Yoshikawa | D06F 35/003 |
| | | | 8/115.6 |
| 2008/0016919 A1 | 1/2008 | Lee | |
| 2008/0023385 A1 | 1/2008 | Baker, Jr. et al. | |
| 2008/0041117 A1 | 2/2008 | Lee | |
| 2008/0085326 A1 | 4/2008 | Ruan | |
| 2008/0131471 A1 | 6/2008 | Kolbe et al. | |
| 2008/0217807 A1 | 9/2008 | Lee et al. | |
| 2008/0248075 A1 | 10/2008 | Brambilla et al. | |
| 2008/0256719 A1 | 10/2008 | Radev | |
| 2008/0276964 A1 * | 11/2008 | Hendrickson | D06F 35/005 |
| | | | 134/18 |
| 2008/0299006 A1 | 12/2008 | Ikemizu | |
| 2008/0302713 A1 | 12/2008 | Patrick | |
| 2009/0000040 A1 | 1/2009 | Ikemizu | |
| 2009/0104239 A1 | 4/2009 | Parsons et al. | |
| 2009/0181592 A1 | 7/2009 | Dugan | |
| 2009/0193593 A1 | 8/2009 | Kirigakubo et al. | |
| 2009/0218266 A1 | 9/2009 | Sawafta et al. | |
| 2009/0259157 A1 | 10/2009 | Thomas | |
| 2010/0000268 A1 | 1/2010 | Kohne | |
| 2010/0047321 A1 | 2/2010 | Sandford et al. | |
| 2010/0050872 A1 | 3/2010 | Lee | |
| 2010/0102002 A1 | 4/2010 | O'Brien et al. | |
| 2010/0116689 A1 | 5/2010 | Greene et al. | |
| 2010/0140185 A1 | 6/2010 | Hill | |
| 2010/0183739 A1 | 7/2010 | Newman | |
| 2010/0193449 A1 | 8/2010 | Shang et al. | |
| 2010/0243432 A1 | 9/2010 | Ikemizu | |
| 2011/0017609 A1 | 1/2011 | Choi | |
| 2011/0094972 A1 | 4/2011 | King et al. | |
| 2011/0100838 A1 | 5/2011 | Kim et al. | |
| 2011/0120921 A1 | 5/2011 | Kim | |
| 2011/0139632 A1 | 6/2011 | Beringer et al. | |
| 2011/0180423 A1 | 7/2011 | Barry et al. | |
| 2011/0224120 A1 | 9/2011 | Meine et al. | |
| 2011/0225741 A1 | 9/2011 | Poy et al. | |
| 2011/0262556 A1 | 10/2011 | Holladay et al. | |
| 2011/0297609 A1 | 12/2011 | Hu | |
| 2012/0003326 A1 | 1/2012 | Meine et al. | |
| 2012/0055862 A1 | 3/2012 | Parekh et al. | |
| 2012/0091070 A1 | 4/2012 | Sjaunta et al. | |
| 2012/0187052 A1 | 7/2012 | Elliott | |
| 2012/0192363 A1 | 8/2012 | King | |
| 2012/0213665 A1 | 8/2012 | Bik et al. | |
| 2013/0022686 A1 | 1/2013 | Rademan et al. | |
| 2013/0146086 A1 * | 6/2013 | Everson | B01J 39/07 |
| | | | 134/10 |
| 2013/0281345 A1 | 10/2013 | Burkinshaw et al. | |
| 2013/0327419 A1 | 12/2013 | Morham | |
| 2014/0202943 A1 | 7/2014 | Pradeep et al. | |
| 2014/0369953 A1 | 12/2014 | Purschwitz et al. | |
| 2014/0377467 A1 * | 12/2014 | George | D06B 3/00 |
| | | | 427/381 |
| 2015/0047718 A1 * | 2/2015 | Brown | G05D 11/132 |
| | | | 137/268 |
| 2015/0159314 A1 | 6/2015 | Morham et al. | |

(56) References Cited

U.S. PATENT DOCUMENTS

| | | | |
|---|---|---|---|
| 2015/0159319 A1 | 6/2015 | Morris et al. | |
| 2017/0008783 A1 | 1/2017 | Brown et al. | |

FOREIGN PATENT DOCUMENTS

| | | |
|---|---|---|
| CN | 1558016 | 12/2004 |
| CN | 1671911 | 9/2005 |
| CN | 2725278 | 9/2005 |
| CN | 2753774 | 1/2006 |
| CN | 2780804 | 5/2006 |
| CN | 200984347 | 12/2007 |
| CN | 101411958 | 4/2008 |
| CN | 201056507 | 5/2008 |
| CN | 101307555 | 11/2008 |
| CN | 201254480 | 6/2009 |
| CN | 101670123 | 3/2010 |
| CN | 101731269 | 6/2010 |
| CN | 101863581 | 10/2010 |
| CN | 101864670 | 10/2010 |
| CN | 101926363 | 12/2010 |
| CN | 101967025 | 2/2011 |
| CN | 201737797 | 2/2011 |
| CN | 201738163 | 2/2011 |
| CN | 101991870 | 3/2011 |
| CN | 201791121 | 4/2011 |
| CN | 201873556 | 6/2011 |
| CN | 201902711 | 7/2011 |
| CN | 202021117 | 11/2011 |
| CN | 202023990 | 11/2011 |
| CN | 202036069 | 11/2011 |
| CN | 102330844 | 1/2012 |
| CN | 202121806 | 1/2012 |
| CN | 102421295 | 4/2012 |
| CN | 102535114 | 7/2012 |
| CN | 202386643 | 8/2012 |
| CN | 202390678 | 8/2012 |
| CN | 102666397 | 9/2012 |
| CN | 202410344 | 9/2012 |
| CN | 202430491 | 9/2012 |
| CN | 102781814 | 11/2012 |
| DE | 19853193 | 5/2000 |
| DE | 102007034215 | 5/2008 |
| EP | 0128782 | 11/1987 |
| EP | 1296895 | 4/2003 |
| EP | 1334073 | 8/2003 |
| EP | 1600545 | 11/2005 |
| EP | 1785518 | 5/2007 |
| EP | 1983085 | 10/2008 |
| EP | 2045389 | 4/2009 |
| EP | 2461676 | 6/2012 |
| EP | 2499916 | 9/2012 |
| EP | 2513370 | 10/2012 |
| EP | 2544804 | 1/2013 |
| EP | 2674523 | 12/2013 |
| GB | 2298858 | 3/1995 |
| GB | 2419590 | 5/2006 |
| JP | H0560721 | 3/1993 |
| JP | 2001025772 | 1/2001 |
| JP | 2001062458 | 3/2001 |
| JP | 2001066090 | 3/2001 |
| JP | 2001276484 | 10/2001 |
| JP | 2001340281 | 12/2001 |
| JP | 2002113288 | 4/2002 |
| JP | 2004057423 | 4/2004 |
| JP | 2004105692 | 4/2004 |
| JP | 2004313752 | 11/2004 |
| JP | 2004346024 | 12/2004 |
| JP | 2005098606 | 4/2005 |
| JP | 2005261830 | 9/2005 |
| JP | 2005296671 | 10/2005 |
| JP | 2007061757 | 3/2007 |
| JP | 2008119287 | 5/2008 |
| JP | 2007167785 | 7/2008 |
| JP | 2008183283 | 8/2008 |
| JP | 2008220450 | 9/2008 |
| JP | 2008279056 | 11/2008 |
| JP | 2009017907 | 1/2009 |
| JP | 2009039320 | 2/2009 |
| JP | 2010136738 | 6/2010 |
| JP | 2010136739 | 6/2010 |
| JP | 2010194484 | 9/2010 |
| JP | 2012161728 | 8/2012 |
| JP | 2014176448 | 9/2014 |
| KR | 1990069099 | 9/1999 |
| KR | 20000037120 | 7/2000 |
| KR | 20020012369 | 2/2002 |
| KR | 20020074306 | 9/2002 |
| KR | 20040085107 | 10/2004 |
| KR | 20040093957 | 11/2004 |
| KR | 20050004614 | 1/2005 |
| KR | 20050004616 | 1/2005 |
| KR | 20050004618 | 1/2005 |
| KR | 20050004620 | 1/2005 |
| KR | 20050004621 | 1/2005 |
| KR | 20050004623 | 1/2005 |
| KR | 20050004625 | 1/2005 |
| KR | 20050004626 | 1/2005 |
| KR | 20050065718 | 6/2005 |
| KR | 20050068357 | 7/2005 |
| KR | 20050089257 | 9/2005 |
| KR | 20070028012 | 3/2007 |
| KR | 100736819 | 7/2007 |
| KR | 100818561 | 4/2008 |
| KR | 20080075694 | 8/2008 |
| KR | 20090001293 | 1/2009 |
| KR | 20090090501 | 8/2009 |
| KR | 20110062719 | 6/2011 |
| KR | 20110075870 | 7/2011 |
| KR | 20120000652 | 1/2012 |
| KR | 101430906 | 8/2014 |
| MD | 2940 | 12/2005 |
| RU | 2135417 | 8/1999 |
| RU | 2182128 | 5/2002 |
| RU | 2193528 | 11/2002 |
| RU | 2264990 | 11/2005 |
| RU | 2324026 | 5/2008 |
| RU | 2373156 | 11/2009 |
| RU | 2381182 | 2/2010 |
| TW | I252268 | 4/2006 |
| TW | 200902790 | 1/2009 |
| TW | 201013008 | 4/2010 |
| TW | 201127948 | 8/2011 |
| TW | 201138638 | 11/2011 |
| UA | 22673 | 4/2007 |
| WO | 1999039749 | 8/1999 |
| WO | 2002036499 | 5/2002 |
| WO | 2003051780 | 5/2003 |
| WO | WO2004003280 A1 | 1/2004 |
| WO | 2004104153 | 12/2004 |
| WO | 2006014080 | 1/2006 |
| WO | 2006129982 | 12/2006 |
| WO | 2007057077 | 5/2007 |
| WO | 2008075992 | 6/2008 |
| WO | 2011015429 | 2/2011 |
| WO | 2011067748 | 6/2011 |
| WO | 2011073697 | 6/2011 |
| WO | 2011110550 | 9/2011 |
| WO | 2011126395 | 10/2011 |
| WO | 2011139835 | 11/2011 |
| WO | 2012025943 | 3/2012 |
| WO | 2012031853 | 3/2012 |
| WO | 2012059992 | 5/2012 |
| WO | 2012077122 | 6/2012 |
| WO | 2012095665 | 7/2012 |
| WO | 2012095828 | 7/2012 |
| WO | 2012107422 | 8/2012 |
| WO | 2012140520 | 10/2012 |
| WO | 2012142025 | 10/2012 |
| WO | 2012150506 | 11/2012 |
| WO | 2012155269 | 11/2012 |
| WO | 2014196881 | 12/2014 |
| WO | 2015001870 | 1/2015 |

(56) References Cited

FOREIGN PATENT DOCUMENTS

WO    2015084568    6/2015
WO    2015084569    6/2015

OTHER PUBLICATIONS

Mitrano et al., "Presence of Nanoparticles in Wash Water from Conventional Silver and Nano-silver Textiles," ACS Nano, 2014, pp. 7208-7219, vol. 8, No. 7.
Putro et al., "Silver Nano Perfume Ejector to Destroy Bacteria for Clothes," AASIC, 2013, pp. 72-75.
Anonymous, "Silvaclean," Jun. 25, 2015, pp. 1-2, Retrieved from the Internet: URL:http://www.medgadget.com/wp-conent/uploads/2015/06/SilvaClean.pdf [retrieved on Mar. 3, 2020].
Fu-Sheng, W. et al., "Spectrophotometric determination of silver with cadion 2B and triton X-100," Talanta, vol. 30, Issue 3, Mar. 1983, pp. 190-192.
Supplementary European Search Report in dated Sep. 6, 2019 in connection with European Patent Application No. 16839836, 60 pages.

* cited by examiner

SYSTEMS AND PROCESSES FOR TREATING TEXTILES WITH AN ANTIMICROBIAL AGENT

CROSS REFERENCE TO RELATED APPLICATIONS

This application is a continuation of U.S. patent application Ser. No. 15/870,944, filed Jan. 13, 2018, now U.S. Pat. No. 10,351,807, which is a divisional application of U.S. patent application Ser. No. 15/085,539, filed Mar. 30, 2016, now abandoned, which claims the benefit of the following U.S. Provisional Patent Applications: U.S. Provisional Patent Application No. 62/297,304, filed Feb. 19, 2016; and U.S. Provisional Patent Application No. 62/208,444, filed Aug. 21, 2015. All of the aforementioned applications are incorporated by reference herein in their entirety.

FIELD

The disclosure is directed to systems and methods for treating textiles with antimicrobial agents.

BACKGROUND

Microbial contamination of textiles can contribute to the spread of infectious diseases, including healthcare associated infections, which are among the leading causes of preventable deaths in the United States and are associated with a substantial increase in health care costs each year. In other instances, microbial contaminations can cause unsightly stains and unpleasant odors.

In one prior approach to providing a textile having antimicrobial properties, the textile is treated with an antimicrobial agent during a textile manufacturing process. For example, the fibers of the textile are embedded or coated with antimicrobial agent during the manufacturing process. However, the total amount of antimicrobial agent is fixed at the point of conversion of the fibers into a textile and the efficacy declines over time as the antimicrobial agent in the fabric is washed away when laundered and never restored. Moreover, this approach has proven to be unsatisfactory to market participants. In addition to the efficacy/performance issues noted above, these products require commercial linen users, such as hospitals and other health care delivery facilities, to make a large upfront capital investment to purchase a new, antimicrobial agent-impregnated, linen inventory and discard existing and otherwise useable inventory. Further, the products may exhibit a soiled off-white discoloration appearance, may be uncomfortable to the touch, and are known to be difficult to launder, dry and press verses traditional linens.

SUMMARY

In one aspect, the disclosure is directed to a method of treating a textile with an antimicrobial agent over a plurality of laundry cycles including a wash cycle and a treatment cycle. The method includes the steps of (a) receiving a textile in a wash system for a first laundry cycle, (b) initiating a wash cycle including a detergent, (c) initiating a post-detergent treatment cycle including dosing the textile with a solution having a predetermined concentration of an antimicrobial agent that includes a metallic ion, and repeating steps (a)-(c) for each of a plurality of additional laundry cycles, wherein the predetermined concentration is insufficient to achieve a predetermined antimicrobial efficacy for the textile due to the first laundry cycle alone but sufficient to achieve the predetermined antimicrobial efficacy for the textile due to a combination of the first laundry cycle and one or more of the plurality of additional laundry cycles. The treatment cycle may be a rinse cycle. The textile may include an inventory of plurality of pieces. The metallic ion may be a silver ion.

In various embodiments of the disclosure, the predetermined antimicrobial efficacy is achieved when the textile is infused with at least approximately 0.6 mg of metallic ion per kg of textile. The plurality of laundry cycles may include at least three cycles to provide the predetermined concentration in the textile. The predetermined concentration is such that a content of the antimicrobial agent infused into the textile is less than approximately 0.5 mg of metallic ion per kg of textile in response to steps (a)-(c) performed for the first laundry cycle. The predetermined concentration is approximately 0.5 mg to approximately 50 mg of antimicrobial agent per kilogram of textile.

In an example method of the disclosure, the textile is dosed with the antimicrobial solution by diluting a concentrated metal ion solution in a container of the wash system containing the textile. The diluting is accomplished by transferring the concentrated metal ion solution to the container at a rate of approximately 1 ml/sec to 30 ml/sec. The concentrate maybe transferred over a dosing period of 15 seconds to 120 seconds. In some instance, the dosing may include different or several dosing rates, for example, transfer rates between about 5 ml/min and about 1000 ml/min.

Another aspect of the disclosure is directed to method for treating a textile with an antimicrobial agent wherein the quality of the water used in the method is taking into consideration. The method includes (a) measuring a quality of a water source for a washing system, (b) providing, in a first container, a first solution having a first predetermined liquid concentration of an antimicrobial agent that includes a metallic ion, such as a silver ion; (c) determining an amount of the first solution to transfer from the first container to the second container based on the measured quality of the water; (d) transferring, from the first container to the second container, the determined amount of the first solution to provide a second solution having a second liquid concentration of the antimicrobial agent in the second container; and (e) submerging the textile in the second solution at least one of prior to, during or after step (d) to infuse the textile with the antimicrobial agent. In one embodiment, steps (a)-(e) may be performed for an initial laundry cycle and steps (b), (d), and (e) are repeating in a plurality of subsequent laundry cycles, In the method, the second solution may include the water from the water source and the first solution. The method may also include providing an amount of the water from the water source to the second container prior to transferring the first solution from the first container to the second container, and measuring the quality of water using a sensor located in the second container. The determined amount of the first solution may be inversely related to the measured quality of the water such that a greater amount of the first solution is determined in response to a measurement of poor quality of water than is determined in response to a measurement of good quality of water. For example, the first predetermined liquid concentration may be approximately 200 PPM to approximately 5000 PPM. Also, the amount of the first solution may be determined such that the second concentration of the second solution is approximately 7.6 PPM (aq) to approximately 115 PPM (aq) responsive to the measured quality of water having a Relative Water Quality (RWQ)

number of approximately 0 RWQ to approximately 5 RWQ. The submerging the textile in the second solution may include agitating the textile for between 30 seconds and 120 seconds.

A further aspect of the disclosure is a method of reducing a microbial load in an inventory of textiles comprising a plurality of pieces at a healthcare facility. The method includes (a) receiving a first portion including a portion of the plurality of pieces of the inventory in a wash basin for a laundry cycle; (b) initiating the laundry cycle including a wash cycle and a treatment cycle, wherein the treatment cycle includes a solution having a predetermined concentration of an antimicrobial agent that comprises a metallic ion; (c) receiving a subsequent portion of the inventory and repeating steps (a) and (b) in a subsequent laundry cycle for the subsequent portion, and repeating step (c) until a predetermined amount of the pieces of the inventory have achieved the predetermined antimicrobial efficacy, thereby reducing the antimicrobial load of the inventory. In various embodiments, the subsequent portion may include a plurality of pieces from the first portion. The predetermined amount of the pieces may include at least 50% of the inventory.

In other embodiments, a single laundry cycle is insufficient to achieve the predetermined antimicrobial efficacy. The predetermined antimicrobial efficacy may be achieved when the textile is infused with at least approximately 1 mg of metallic ion per kg of textile.

In yet another aspect, the disclosure is directed to a method of protecting individuals in contact with healthcare facility linen inventory from a healthcare acquired infection. The method includes (a) receiving, in one or more batches at a healthcare facility, an inventory of washable, non-disposable textiles that contact patients and healthcare workers; (b) washing each batch using a detergent; and (c) for each batch, after washing the batch, treating the batch with a solution including a predetermined liquid concentration of a metallic ion to reduce the microbial load on the textiles in the batch and improve a resistance of the textiles in the batch to microbial contamination responsible for a healthcare acquired infections. The predetermined concentration may be such that a content of the antimicrobial agent infused into each textile is less than approximately 0.5 mg 0.75 mg of metallic ion per kg of textile in response to (c) performed during an initial laundering process and the method further includes repeating steps (a)-(c) at least once to incrementally increase the content of the antimicrobial agent infused into each textile to greater than 1 mg of metallic ion per kg of textile. The solution may include water treated by deionization or reverse osmosis.

In various embodiments, the method may include treating clean textiles that have not entered the healthcare facility. Textiles may be a mixture of clean textiles and soiled textiles. The predetermined concentration of metallic ion may be achieved in a single treatment or the predetermined concentration of the metallic ion may be achieved after two or more treatments.

Still further, the disclosure is directed to a method of infusing textiles with an antimicrobial agent. The method includes (a) providing a tunnel washer having an intake, a discharge, and a plurality of modules that segment an interior of the tunnel washer between the intake and the discharge, wherein the plurality of modules include an initial module at the intake a final module at the discharge; (b) moving the textile from the intake to the discharge through the plurality of modules; (c) washing the textile with a detergent at a wash module of the plurality of modules; (d) after washing the textile at the first module, rinsing the textile at a rinse module of the plurality of modules; and (e) treating the textile with a solution having a predetermined concentration of an antimicrobial agent at a treatment module, wherein the antimicrobial agent includes a metallic ion. The method may further include (f) extracting excess fluid, including at least a portion of the solution, from the textile after the treatment module; and (g) providing at least a portion of the extracted excess fluid to at least one of the rinse module or the wash module for processing a subsequent textile. The solution may include water treated by distillation, deionization or reverse osmosis.

Even further, the disclosure is directed to a method of reducing the amount of silver required to reduce the antimicrobial burden in a textile subjected to a repeated wash cycles. The method includes, following a plurality of the wash cycles, treating the textile in a treatment cycle including a solution having predetermined concentration of an antimicrobial agent that includes a metallic ion, wherein the predetermined concentration is insufficient to achieve a predetermined antimicrobial efficacy for the textile in a first treatment cycle but sufficient to achieve the predetermined antimicrobial efficacy for the textile due to a combination of a first treatment cycle and one or more of the plurality of additional treatment cycles.

Another aspect of the disclosure is directed to a method for detecting the presence of silver in a textile. The method includes dispensing a first solution and the second solution onto separate areas of the textile and comparing the color of the dispensed first solution and the dispensed second solution. The first solution includes Cadion B, a buffer sufficient to maintain a pH in the range of from about 8 to about 10, and a surfactant. The second solution comprises Cadion B, a buffer sufficient to maintain a pH in the range of from about 8 to about 10, a surfactant, and a complexing agent, wherein formation of a complex of the complexing agent and silver is a more favorable than formation of a complex of Cadion B and silver. One or both solutions may also include a masking agent, such as ethylenediaminetetraacetic acid (EDTA) or cyclohexanediaminetetraacetic acid (CDTA). One or both solutions may also include a water-miscible organic solvent, such as 1-methyl-2-pyrrolidinone. The complexing agent may be sodium thiosulfate. The surfactant may be TWEEN® 20 or TRITON™ X-100. The buffer may include one or more of potassium tetraborate, citric acid, and sodium citrate.

Figure 1:
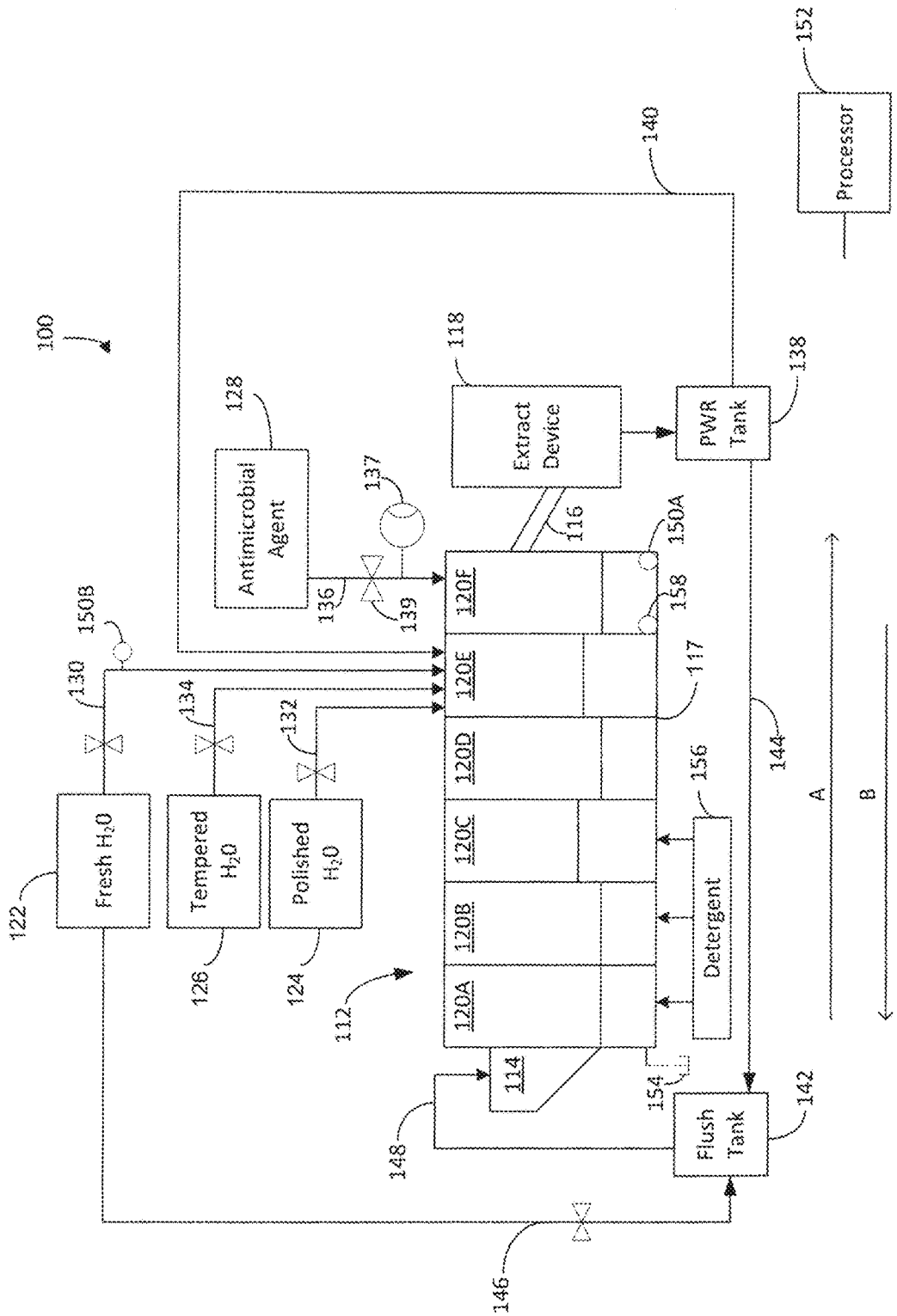
FIG. 1 is a simplified block diagram of an example washer system according to aspects of the disclosure.

While the invention is susceptible to various modifications and alternative forms, specific embodiments have been shown by way of example in the Figures and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims. It should be understood that other embodiments may include more or less of each element shown in a given Figure. Further, some of the illustrated elements may be combined or omitted. Yet further, an example embodiment may include elements that are not illustrated in the Figures.

DESCRIPTION

The following description describes various features and functions of the disclosed systems and methods with reference to the accompanying figures. In the Figures, similar symbols typically identify similar components, unless context dictates otherwise. The illustrative systems and methods described herein are not meant to be limiting. It will be readily understood that certain aspects of the disclosed systems and methods can be arranged and combined in a wide variety of different configurations, all of which are contemplated herein.

According to aspects of the disclosure, systems and processes are described and illustrated for treating textiles with an antimicrobial agent. The terms fabric, linen, and textile are used interchangeably herein. Aspects of the disclosure may be described in the context of a single textile for ease of description; however, it should be understood that such aspects can be extended to include processes and devices in the context of multiple textiles such as an inventory of textiles having multiple pieces.

The systems and processes for treating textiles with the antimicrobial agent can mitigate healthcare associated infections (HAIs). HAIs are infections that people acquire while they are receiving treatment in a health care setting for other ailments. HAIs may be caused by any infectious agent, including bacteria, fungi, and viruses, as well as other less common types of pathogens. HAIs can be acquired anywhere health care is delivered, including inpatient acute care hospitals, outpatient settings such as ambulatory surgical centers and end-stage renal disease facilities, and long-term care facilities such as nursing homes and rehabilitation centers. In addition, those persons in contact with soiled laundry from a healthcare facility, including care givers and persons in the laundry supply chain, are at risk of infection.

The disclosure is also related to treating textiles from other sources other than health care facilities. For example, garments worn by sports teams are known for harboring infection agents. In essence, the devices and method of the disclosure can be used to treat textiles from any source that could benefit from lowering of the microbial content of the textiles.

Accordingly, one aspect of the disclosure is directed to method of treating a textile with an antimicrobial agent over a plurality of laundry cycles including a wash cycle and a post-wash/post-detergent treatment cycle that provides for dosing the textile with a solution having a predetermined concentration of an antimicrobial agent that includes a metallic ion, such as for example a silver ion. In this aspect, the predetermined concentration of the agent is insufficient to achieve a predetermined antimicrobial efficacy for the textile due to the first laundry cycle alone but sufficient to achieve the predetermined antimicrobial efficacy for the textile due to a combination of the first laundry cycle and one or more additional laundry cycles. The laundry cycle may include additional cycles, for example a prewash cycle, a rinse cycle, or the treatment cycle may be combined with the rinse cycle.

In an example method of the disclosure, the textile is dosed with the antimicrobial solution by diluting a concentrated metal ion solution in a container of the wash system containing the textile. The diluting is accomplished by transferring the concentrated metal ion solution to the container at a rate of approximately 1 ml/sec to 30 ml/sec. The concentrate maybe transferred over a dosing period of 15 seconds to 120 seconds. In some instance, the dosing may include different or several dosing rates, for example, transfer rates between about 5 ml/min and about 1000 ml/min.

The method for treating a textile with an antimicrobial agent may include consideration of the water quality used in an antimicrobial solution and/or the treatment bath. Accordingly, the quality of a water source for the washing system may be determined, for example, in association with providing a first solution having a first predetermined liquid concentration of an antimicrobial agent that includes a metallic ion to a first container. For example, a concentrated silver ion solution may be added to a first container to create a first solution. The amount of the first solution that is transferred from the first container to a second container to create a second solution, for instance the treatment bath, is determined based on the measured quality of the water. The determined amount of the first solution is used to create the second solution with a second liquid concentration of the antimicrobial agent in the second container. The textile is submerged in the second solution (or precursor) prior to, during and/or after the solution is created in or provided to the second container. For example, the first solution is added to a rinse solution that includes the textiles, or the rinse solution may be replaced in the container with the second solution. Water from the water source may be provided to the second container prior to transferring the first solution from the first container to the second container. A sensor may be located in the second container to measure the quality of the water provided in the second container. When water quality is consistent, the determination and use of the water quality in a first laundry cycle may be used in second or subsequent cycles.

The determined amount of the first solution may be inversely related to the measured quality of the water such that a greater amount of the first solution for use in the second solution is determined in response to a measurement of poor quality of water than is determined in response to a measurement of good quality of water. In some embodiment, the second solution may include the water from the water source and the first solution. The amount of the first solution may be determined such that the second concentration of the second solution is approximately 7.6 PPM (aq) to approximately 115 PPM (aq) responsive to the measured quality of water. For example, the first predetermined liquid concentration may be approximately 200 PPM to approximately 5000 PPM. At least one of the first solution or the second solution may include water treated by distillation, deionization or reverse osmosis.

The time that the textile spends in the second solution depends on a number of factors including concentration of anti-microbial agent in the solution, water quality, and textile type. From a commercial perspective, the textile should spend as little as time as possible to achieve the desired level of antimicrobial agent in the textile. For example, the textile may spend between 30 seconds and 120 seconds, which may include agitation.

Another aspect of the disclosure involves a method of reducing a microbial load in an inventory of textiles including a plurality of pieces at a healthcare facility. Pieces refers to individual gowns, sheet, towels, uniforms, lab coats and other textiles associated with the facility. The method receiving a first portion of the plurality of pieces of the inventory in a wash basin for a laundry cycle, which includes a wash cycle and a treatment cycle. The treatment cycle includes submerging the textiles in a solution having a predetermined concentration of an antimicrobial agent that includes a metallic ion, for example a silver ion. The method also includes receiving a subsequent portion of the inventory, which may include pieces from the first portion of the inventory, and repeating step laundry cycle. Regular treatment of portions of a textile inventory will result in all, almost all, most or many of the pieces of the inventory achieving an antimicrobial efficacy, thereby reducing the antimicrobial load of the inventory. In general, a predetermined number of pieces or percentage of the inventory can be defined as requiring a predetermined amount of antimicrobial efficacy. For example, regular treatment of portions of an inventory can result in at least 50%, at least 75%, at least 85%, at least 95%, at least 99%, or 100% of all of the pieces of textile in inventory achieving a predetermined level of antimicrobial efficacy. In one example the predetermined antimicrobial efficacy may be achieved when the textile is infused with at least approximately 1 mg of metallic ion per kg of textile.

Methods of the disclosure require the use of the antimicrobial solution, which may be supplied to the laundry facility in several ways. A supplier can deliver pre-prepared dilute solutions for direct addition to a treatment cycle, or the supplier can deliver a concentrate that may require dilution before addition to a treatment cycle. In addition, solutions may be created on-site using a variety of known methods for creating metallic ion solutions. Suppliers of wash chemistry often provide instructions, hardware and software for implementing laundry cycles. Accordingly, in one aspect, the disclosure is directed to a method for treating a textile with an antimicrobial agent that includes providing an antimicrobial solution to a laundry facility and instructing the facility on a method for treating the textiles as described herein. For instance, the instruction may include the steps for treating a textile with an antimicrobial agent over a plurality of laundry cycles including a wash cycle and a post-wash/post-detergent treatment cycle that provides for dosing the textile with a solution having a predetermined concentration of an antimicrobial agent that includes a metallic ion, such as for example a silver ion. In this aspect, the instructions may provide the parameters for a predetermined concentration of the agent in the treatment cycle that is insufficient to achieve a predetermined antimicrobial efficacy for the textile due to the first laundry cycle alone but sufficient to achieve the predetermined antimicrobial efficacy for the textile due to a combination of the first laundry cycle and one or more additional laundry cycles. The instructions may also include information regarding rates of addition of ion solutions to the treatment bath.

The instructions can include steps for monitoring water quality associated with a process for treating textiles with an antimicrobial agent. As an example, the disclosure is directed to the delivery of an antimicrobial agent to a laundry facility with instructions for treating textiles to a with the antimicrobial agent, wherein the instructions include steps for measuring the quality of the facilities water source and for adjusting the concentration of the antimicrobial agent in a treatment cycle based upon the quality of the water. The instructions may also include steps for treating an inventory of laundry from a healthcare facility, wherein the steps include receiving portions of the healthcare facilities laundry inventory and processing those portions until a predetermined number of pieces of the inventory achieve a predetermined antimicrobial efficacy. The instructions may include the predetermined number of pieces and the predetermined efficacy.

The disclosure is applicable to all types of laundry systems. For example, the systems and processes of the disclosure can be utilized to treat an inventory of washable, non-disposable textiles in a batch by batch process. For instance, batch-type laundry systems are described in U.S. Pat. No. 8,641,967, U.S. Patent Appl. Publication No. 2015/0159314, Patent Appl. Publication No. 2015/0159319, Patent Appl. Publication No. 2015/0047718, and U.S. application Ser. No. 13/968,084 filed Aug. 15, 2013, which are incorporated by reference in their entirety.

In an exemplary aspect, a washer system includes a continuous batch washer (i.e., tunnel washer) that implements or improves antimicrobial treatment of a textile during a laundry cycle. The tunnel washer includes an intake, a discharge, and a plurality of modules that segment an interior of the tunnel washer between the intake and the discharge. The plurality of modules include at least one wash module in which the textile is washed with a detergent and at least one rinse module in which the textile is rinsed after being washed. A rinse module or a last module before the discharge may be a treatment module in which the textile is treated with an antimicrobial agent. By treating the textile with the antimicrobial agent in the rinse module or a last module before the discharge, greater amounts of antimicrobial agent are retained by the textile upon completion of the laundry cycle. This is, in part, because treating the textile in the rinse module or a last module mitigates leaching of antimicrobial agent content from the textile, which would otherwise occur if the textile was treated before or during a wash cycle. Further advantage may be obtained by treating the textile with the antimicrobial agent in a last module after a rinse cycle to ensure that some of antimicrobial agent is not rinsed away.

In some additional or alternative aspects of the disclosure, after treating the textile, the textile is subjected to an extraction device operable to extract fluids, for example rinse water, from the textile. The extracted fluids may contain excess antimicrobial agent that was not infused into the textile. Advantageously, the washer system may recirculate the extracted fluids back into the tunnel washer so as to substantially reduce (or eliminate) wasted antimicrobial agent. Additionally, recirculating the extracted fluids reduces the amount of antimicrobial agent content in waste water effluent, thus mitigating the extent to which waste water effluent needs to be treated to comply with environmental regulations. In some implementations, at least a portion of the extracted fluid is provided to a rinse module. In additional or alternative implementations, at least a portion of the extracted fluid is provided to other areas of the tunnel washer such as, for example, the intake or a pre-wash module. In further additional or alternative implementations, at least a portion of the extracted fluid is provided to the treatment module.

In further additional or alternative aspects of the disclosure, the washer system can measure a quality of the water and, based on the measured water quality, determine a dosage or concentration of antimicrobial agent in a treatment cycle for treating the textile. The washer system may then controllably adjust an amount of antimicrobial agent in the treatment cycle to achieve the determined dosage and treat the textile. In this way, problems associated with poor or changed water quality can be mitigated during treatment of the textile from batch to batch, day to day, and so on.

According to additional or alternative aspects of the disclosure, a process for treating a textile with an antimicrobial agent is provided. In particular, a process is provided for incrementally loading a textile to an efficacious antimicrobial content level over multiple laundry cycles. This approach provides substantial cost savings over the useful life of the textile as compared to existing antimicrobial treatment approaches. For instance, the typical useful life of a linen processed in a commercial laundry may be less than 35 wash cycles. Over the life of the linen, the process requires less antimicrobial agent to maintain the antimicrobial efficacy than other approaches.

Referring now to FIG. 1, a simplified block diagram of an example washer system 100 is illustrated according aspects of the disclosure. As shown in FIG. 1, the washer system 100 includes a tunnel washer 112 having an intake 114 at a first end and a discharge 116 at a second end. The intake 114 receives one or more textiles to be washed and treated. In one example, the intake 114 can be in the form of a hopper that can receive a batch of textiles into the tunnel washer 112. The discharge 116 facilitates transferring clean, treated textiles from the tunnel washer 112 to a fluid-extraction device 118. In one example, the discharge 116 can be in the form of a slide or a chute that transports the washed textiles towards the fluid-extraction device 118. In another example, the discharge 116 can include a receptacle for holding the washed textiles until the fluid-extraction device 118 is ready to receive the washed textiles. The fluid-extraction device 118 can be, for example, a centrifugal extractor and/or a mechanical press.

The tunnel washer 112 includes an outer housing 117, which defines an interior of the tunnel washer 112. The interior of the tunnel washer 112 is segmented by a plurality of modules 120A-120F between the intake 114 and the discharge 116. In the illustrated example, the modules 120A-120F are formed as a plurality of rotating drums separated from each other by lateral side walls.

During operation, the textiles to be washed and treated sequentially move through the modules 120A-120F in the direction of arrow A, entering the outer housing 117 at the intake 114 and exiting the outer housing 117 at the discharge 116. To do so, the modules 120A-120F transfer textiles from one module to the next by a top transfer arrangement and/or a bottom transfer arrangement. For example, the drums may have inlets and outlets on opposing sides of the drums so that the textiles may be transferred through the outlet in one drum into the inlet in the next drum. In some implementations, each drum can further include a scoop-like member mounted within the drum to facilitate transferring the textiles via the inlets and outlets. The scoop-like members can be configured such that oscillating the drums within a limited range of rotation does not transfer the textiles between drums, but instead imparts mechanical action to the textiles to promote the wash and treatment process. However, when the drums are rotated beyond the limited range of rotation, the scoop-like members receive and transport the textiles to the outlets of the drums. In this way, the textiles entering the tunnel washer 112 at the intake 114 are transported through each of the modules 120A-120F in sequence to the discharge 116.

Although the modules 120A-120F are described as rotating drums in the above example, it should be understood that the modules 120A-120F can be formed in other ways such as, for example, by an Archimedean screw within the outer housing 117. Additionally, it should be understood that the modules 120A-120F can have a single-drum construction (i.e., a single drum containing both the fluids and the textiles), a double-drum construction (i.e., each module has a stationary, exterior drum to hold fluids and a rotating, perforated inner drum to move textiles in the fluids), or a combination of single- and double-drum constructions.

In practice, the tunnel washer 112 can include one or more pre-wash modules, one or more main wash modules, one or more rinse modules, one or more neutralization modules, and/or one or more treatment modules according to aspects of the disclosure. The pre-wash module(s) define a pre-wash zone of the tunnel washer 112, the main wash module(s) define a main wash zone, the rinse module(s) define a rinse zone, the neutralization module(s) define a neutralization zone, and the treatment module(s) define a treatment zone of the tunnel washer 112. The number of modules utilized to form these zones in the tunnel washer 112 may vary in different example implementations.

In the illustrated example, the tunnel washer 112 has a pre-wash zone provided by the intake 114 as described in further detail below. The pre-wash zone facilitates initial wetting of the textiles and, optionally, applying heat and wash chemistry early in the process to remove soil from the textiles prior to entering the main wash zone. The tunnel washer 112 has a main wash zone formed by a first module 120A, a second module 120B, and a third module 120C. The modules 120A-120C of the main wash zone may apply heat, steam, wash agents (e.g., a detergent, alkali, bleach, etc.), and/or mechanical action to facilitate removing soil from the textiles. The tunnel washer 112 next includes a rinse zone formed by a fourth module 120D and a fifth module 120E. The modules 120D-120E of the rinse zone facilitate removing residual wash agents carried over during transfer of the textiles from the main wash zone. The tunnel washer 112 lastly includes a treatment zone formed by a sixth module 120F in which the textiles are treated with the antimicrobial agent.

By treating the textile with the antimicrobial agent in the last module 120F before the discharge 116, greater amounts of antimicrobial agent are retained by the textile upon completion of the laundry cycle. This is, in part, because treating the textile in the last module 120F mitigates leaching of antimicrobial agent content from the textile, which would otherwise occur if the textile was further washed or rinsed after being treated with the antimicrobial agent. In other embodiments, the rinse module and treatment module are combined, such that rinsing the textiles and treating the textiles with an antimicrobial agent occurs in the same module or modules. Indeed, in some aspects, the solution used to treat the textiles also performs the functions of a rinse to remove residual wash agents from the textiles.

Although the illustrated example has six modules, it should be understood that the tunnel washer 112 can have more or fewer modules according to alternative aspects of the disclosure. For instance, in some alternative examples, the tunnel washer 112 can have eight to twelve modules. It also should be understood that, in some alternative examples, the pre-wash functions can be provided in one or more pre-wash module(s) instead of the intake 114. And it should be understood that, in some alternative examples, the tunnel washer 112 can include a neutralization zone, between the rinse zone and the treatment zone, to facilitate neutralizing residual alkali, detergent, and/or bleach carried over during transfer of the textiles from the rinse zone. In some examples, the neutralization zone may be further utilized to apply a softener and/or starch to the textiles.

To facilitate adding, removing, and/or transferring water and chemicals in the modules 120A-120F, the tunnel washer 112 can include one or more drains, water sources, chemical sources, fluid tanks, flow lines, valves, pumps, nozzles, and/or weir plates. In the illustrated example, the washer system 100 includes a fresh water source 122, a polished water source 124, and a tempered water source 126. The fresh water source 122 can provide, for example, cold fresh water (e.g., water supplied by a municipality). The polished water source 124 can provide water treated by one or more filtration processes such as, for example, a deionization process, a reverse osmosis process, a granulated activated carbon (GAC) filtration process, a distillation process, or a combination thereof. The tempered water source 126 can provide water that has been heated, for example, to a temperature between approximately 85 degrees Fahrenheit and approximately 100 degrees Fahrenheit (i.e., between approximately 29 degrees Celsius and 43 degrees Celsius).

Also, in the illustrated example, a flow line 130 provides fresh water from the fresh water source 122 to the fifth module 120E, a flow line 132 provides polished water from the polished water source 124 to the fifth module 120E, and a flow line 134 provides tempered water from the tempered water source 126 to the fifth module 120E. Although the flow lines 130, 132, 134 are illustrated as separate from one another, one or more of the flow lines 130, 132, 134 may be coupled so as to provide a mixture of fresh water, polished water, and/or tempered water to the fifth module 120E in other examples. In general, the amount and/or composition of fluid supplied by the sources 122, 124, 126 at a given time may be based on various criteria such as, for example, a measurement of an amount of total dissolved solids (TDS), a hardness, an anions species, etc. by one or more sensors (not shown) in one or more modules 120A-120E.

To supply the modules 120A-120D with fluids, the tunnel washer 112 counterflows fluids from the fifth module 120E towards the intake 114. In this way, the textiles continuously encounter cleaner fluids as the textiles are progressed through the tunnel washer 112 from the intake 114 to the discharge 116. Depending on the construction of the modules 120A-120E, the tunnel washer 112 may transfer fluids by direct counterflow (e.g., fluid flowing through or over lateral side walls due to gravity) and/or indirect counterflow (e.g., via external flow lines and pumps between the modules 120A-120E). Commercially available examples of indirect counterflow systems are the CBW® Tunnel Washer and the PBW® Tunnel Washer, including PULSEFLOW® technology (Pellerin Milnor Corporation, Kenner, La.).

In the illustrated example, a combination of direct counterflow and indirect counterflow can be employed to achieve example fluid levels shown in FIG. 1 for each module 120A-120E. In particular, direct counterflow is utilized for transferring fluids within the rinse zone and for transferring fluids within the main wash zone, whereas indirect counterflow is utilized for transferring fluids from the treatment zone or rinse zone to the main wash zone. This arrangement may help to separate the rinse and wash zones.

In one non-limiting implementation of the illustrated example, the fluid within the fifth module 120E can counterflow back to the fourth module 120D via a weir plate (not shown). The fluid within the fourth module 120D can counterflow back to the third module 120C via a pump (not shown). Using a pump allows the fluid level in the third module 120C to be higher than the fluid level in the fourth module 120D, as shown in FIG. 1. The fluid in the third module 120C then can counterflow back to the second module 120B and the fluid in the second module 120B can counterflow back to the first module 120A via weir plates. The first module 120A may include a weir plate that facilitates transferring excess fluids in the first module 120A to a drain 154. It should be understood that other example implementations for counterflowing fluids from the fifth module 120E to the first module 120A are possible.

The washer system 100 also includes an antimicrobial agent source 128. The antimicrobial agent source 128 can include any device suitable for holding and/or supplying an antimicrobial agent to the tunnel washer 112. Example devices and processes for supplying the antimicrobial agent to the tunnel washer 112 are described in U.S. Pat. No. 8,641,967, U.S. Patent Appl. Publication No. 2015/0159314, Patent Appl. Publication No. 2015/0159319, Patent Appl. Publication No. 2015/0047718, and U.S. application Ser. No. 13/968,084 filed Aug. 15, 2013, the contents of which are incorporated by reference in their entirety. In some of such examples, the antimicrobial source 128 may dilute the antimicrobial agent from a first concentration to a second, lower concentration prior to supplying the antimicrobial agent to the tunnel washer 112. In other examples, the antimicrobial agent can be received in the antimicrobial agent source 128 in the same concentration in which it is supplied to the tunnel washer 128.

In some aspects, the antimicrobial agent can include a metallic ion such as, for example, silver ions. For instance, the antimicrobial agent can include silver nitrate, silver acetate, silver oxide, silver chloride, silver carbonate, silver sulfate, etc. One benefit to using an antimicrobial agent including silver ions is that such antimicrobial agents may cause less skin irritation and may be less detectable by a user than other antimicrobial agents. Nonetheless, it should be understood that other antimicrobial agents can be utilized such as, for example, other metallic ions (e.g., copper, zinc, etc.). The washer system 100 further includes a flow line 136 for providing an antimicrobial solution from the antimicrobial agent source 128 to the sixth module 120F. The antimicrobial solution may include a concentration of antimicrobial agent. A flow meter 137 and a flow control device 139 can be coupled to the flow line 136 to respectively monitor and control the amount of antimicrobial solution (and, thus, the amount of antimicrobial agent) that is provided from the antimicrobial source 128 to the sixth module 120F. The flow control device 139 can include, for example, a peristaltic pump, a diaphragm pump, a solenoid valve, etc.

The sixth module 120F may be initially filled with a combination of fresh water and antimicrobial solution from the fresh water source 122 and the antimicrobial agent source 128, respectively. A flow line from the fresh water source 122 to the sixth module 120F is omitted for clarity of illustration. After the initial setup, additional fluids may be supplied to the sixth module 120F via the transfer of textiles from the fifth module 120E and the antimicrobial agent source 128.

In one aspect, the antimicrobial solution from the antimicrobial agent source 128 is added to fresh water or other process water in the treatment module 120F. The concentration of the antimicrobial agent (i.e., the dosage of antimicrobial agent) applied to textiles in the module 120F may be expressed in terms of mg of antimicrobial agent per Kg of textile in the module 120F (i.e., a dry weight concentration) or, alternatively, in terms of parts per million (PPM) in an aqueous solution (i.e., a liquid concentration). In some examples, the antimicrobial solution can be controllably added to the module 120F to achieve a concentration of approximately 0.5 to approximately 50 mg of antimicrobial agent per 1 Kg of textile in the module 120F. In other examples, the antimicrobial agent can be applied to textiles at a concentration greater than approximately 8 mg antimicrobial agent per 1 Kg of textile and, in still other examples, a concentration greater than approximately 10 mg antimicrobial agent per 1 Kg of textile.

In some implementations, the concentration utilized for a particular batch of textiles may be based on the type of textile materials in the batch as different materials may have different uptake yield rates, which reflects the percent of the antimicrobial agent that becomes associated with the textile during the treatment. Table 1 illustrates example yields for example dosages of textiles of different materials.

TABLE 1

| Linen Type | Batch | Dosage (mg/kg) | Silver Content (mg/kg) | | | | Yield (%) |
|---|---|---|---|---|---|---|---|
| | | | 1 | 2 | 3 | AVG | |
| Cotton | Lot 1 | 1 | 1.1 | 0.8 | 1.3 | 1.1 | 107 |
| | Lot 2 | 1 | 0.7 | 0.8 | 0.7 | 0.7 | 73 |
| | Lot 3 | 1 | 0.7 | 0.7 | 0.8 | 0.7 | 73 |
| Cotton/Poly Blend | Lot 1 | 1.5 | 1.1 | 1.0 | 1.1 | 1.1 | 71 |
| | Lot 2 | 1.5 | 0.9 | 1.9 | 2.9 | 1.9 | 127 |
| | Lot 3 | 1 | 0.9 | 0.9 | 0.9 | 0.9 | 90 |
| Spandex | Lot 1 | 3.4 | 1.4 | 1.6 | 1.6 | 1.5 | 45 |
| | Lot 2 | 3.4 | 1.5 | 1.7 | 1.6 | 1.6 | 47 |
| | Lot 3 | 3.4 | 1.6 | 1.6 | 1.6 | 1.6 | 47 |
| Polyester | Lot 1 | 3.4 | nd | 0.6 | nd | 0.6 | 18 |
| | Lot 2 | 3.4 | 0.7 | 0.8 | 0.6 | 0.7 | 21 |
| | Lot 3 | 3.4 | 1 | 0.9 | 0.9 | 0.9 | 27 |
| | Lot 4 | 4 | 0.9 | 0.9 | 0.9 | 0.9 | 23 |
| Nylon Spandex Blend | Lot 1 | 35 | 1.6 | 1.8 | 1.5 | 1.6 | 5 |
| | Lot 2 | 35 | 1.4 | 1.3 | 1.4 | 1.4 | 4 |
| | Lot 3 | 35 | 1.2 | 1.4 | 1.3 | 1.3 | 4 |
| 100% Nylon | Lot 1 | 35 | 0.9 | 0.9 | 0.9 | 0.9 | 3 |
| | Lot 2 | 35 | 0.9 | 0.8 | 0.8 | 0.8 | 2 |
| | Lot 3 | 35 | 1 | 0.9 | 1.1 | 1.0 | 3 |
| 100% Microfiber | Lot 1 | 35 | 0.7 | 0.6 | 0.7 | 0.7 | 2 |
| | Lot 2 | 35 | 0.5 | 0.6 | 0.6 | 0.6 | 2 |
| | Lot 3 | 35 | 0.9 | 0.8 | 0.7 | 0.8 | 2 |

In Table 1, the dosage reflects the amount of silver ion per kg of textile in the each batch of a treatment cycle a pilot plant study. Silver nitrate was added in an amount that provides the appropriate ion weight. The volume of batch liquid was approximately 25 liters and the amount of the textile was approximately 0.25 kg. It should be understood that Table 1 reflects exemplary dosage values that can be used for the textile materials shown, and other dosages are contemplated For example, in some implementations, a batch of textiles of a particular material may be dosed at a dosage value that differs by about plus or minus 50% from the dosage value listed in Table 1 for the same material, depending on the desired silver content of the treated textile and/or the target antimicrobial efficacy sought to be achieved. Other example implementations are also possible.

In general, the volume of the liquid in each batch is not critical to the antimicrobial update (yield) by the textile. Typically, industrial applications involve treatment batch sizes of about 500-1000 liters, for example about 600 L, for textile loads of about 150 kg. It has been found that moderate adjustment of the liquid volume of the treatment batch does not substantially affect yield.

The rate of addition of the antimicrobial solution to the module can be controlled to ensure that all of the textile in the module is uniformly treated. In some examples, the treatment cycle lasts between about 30 seconds and about 2.5 minutes. Therefore, to achieve a uniform dose of agent throughout the textile load, the addition of the antimicrobial solution to the module may be affected prior to the first 90 seconds of the treatment cycle.

In some aspects, the antimicrobial solution is added to the module at a fixed rate. As one example, the antimicrobial solution having a concentration of about 2,000 PPM (aq) to about 15,000 PPM (aq), more particularly about 4000-15000 PPM, is added to a treatment module containing about, for example, 600 liters of liquid and 150 Kg of textile at a rate of about 30 ml/minute for about 2.5 minutes. In other examples, the antimicrobial agent can be added to the module at a rate between about 5 ml/min to about 50 ml/min for a period of time between about 15 seconds to about 150 seconds. In one particular non limiting example, a 600 liter liquid bath having a liquid antimicrobial agent concentration of 2 PPM (aq) is achieved by adding a 1000 ml solution having an agent concentration of 1,200 PPM for 2.5 minute at rate of 400 ml/min. At this concentration, assuming a theoretical 100% yield, the textiles would be infused with 8 mg/kg of antimicrobial agent.

In other aspects, the antimicrobial solution is added to the module at a variable rate, which further improves the uniformity of the antimicrobial agent on the finished textile. In one example, the antimicrobial agent can be added to the module containing 600 liters of liquid at a rate of about 5 ml/min for about 15 seconds to about 60 seconds followed by a rate of about 20 ml/min for about 15 seconds to about 90 seconds.

As noted above, after the textiles are treated in the sixth module 120F, the textiles are transferred to the fluid-extraction device 118 via the discharge 116. The fluid-extraction device 118 extracts fluids from the textiles. In some examples, the extracted fluids may be drained as waste water effluent. One problem with such an approach is that the extracted fluids may contain excess antimicrobial agent that was not retained within the textiles. If the effluent is not treated, the excess antimicrobial agent may be released into waterways. Above certain concentrations, antimicrobial agents may be a problematic pollutant for many fresh- and salt-water organisms. For this reason, many governmental regulations require operators to treat effluent if the concentration of antimicrobial agent is greater than a proscribed limit (e.g., 10 mg per kg). Unfortunately, effluent treatment can be prohibitively expensive for many laundry operators. Additionally, in some instances, draining the extracted fluids may unnecessarily waste substantial amounts of antimicrobial agent, increasing the cost to treat textiles.

According to some aspects of the disclosure, the washer system 100 can address these problems associated with excess antimicrobial agent in the extracted fluids. In particular, the washer system 100 can collect the extracted fluids from the fluid-extraction device 118 and recirculate the extracted fluids back into the tunnel washer 112. Advantageously, recirculating the extracted fluids mitigates wasted antimicrobial agent and the extent to which waste water effluent needs to be treated to comply with environmental regulations.

In the illustrated example, the extracted fluids are collected in a press-water-recovery (PWR) tank 138. As shown in FIG. 1, the PWR tank 138 can provide at least a portion of the extracted fluid to the fifth module 120E in the rinse zone via a flow line 140. Providing antimicrobial agent (e.g., silver ions) to a module 120E preceding the treatment module 120F may allow the antimicrobial agent to bind or chelate to contaminants or other inhibiting ions in the fluid of module 120E, thereby facilitating a more accurate treatment of the textiles in the treatment module 120F. Additionally, providing the antimicrobial agent to the module 120E may facilitate greater uniformity of antimicrobial agent distribution in the textiles.

Also, as shown in FIG. 1, the PWR tank 138 can also provide at least a portion of the extracted fluid to a flush tank 142 via a flow line 144. The flush tank 142 may also receive fresh water from the fresh water source 122 via a flow line 146. The flush tank 142 may then provide a mixture of fresh water and the extracted water (which may contain excess antimicrobial agent) to the intake 114 via a flow line 148. In this way, the flush tank 142 can provide fluids to the intake 114, which allow the intake 114 to function as a pre-wash module when textiles are received in the intake 114. Providing the antimicrobial agent in the intake 114 can facilitate uniformity of antimicrobial agent distribution and more accurate treatment of the textiles in subsequent modules. In general, increasing the number of exposures of the textile to the antimicrobial agent can facilitate improving the uniformity of antimicrobial agent distribution in the textile.

To provide the extracted fluids to the fifth module 150E and/or the flush tank 142, the washer system 100 can include one or more pumps and/or valves (which are not shown for clarity of illustration). Although the extracted fluids may be provided to the intake 114 and/or the fifth module 120E in the illustrated example, it should be understood that the extracted fluids can be similarly provided to other modules in other examples. For instance, in another example, at least portion of the extracted fluids can be additionally or alternatively provided by the PWR tank 138 to the sixth module 120F in the treatment zone.

According to additional or alternative aspects of the disclosure, the washer system 100 can include additional features that help to mitigate problems associated with poor water quality. During the treatment process, the metallic ions of the antimicrobial agent may attach to a textile via electrostatic dipole interactions or other interactions including mechanical interaction. For some fabrics, the positive charge from the metallic ions is attracted to the slight-negative dipole on the polymer backbone of textile fibers. Generally, contaminants present in poor quality water reduce the probability that the antimicrobial metallic ions will affix to bonding sites of the textile. This is, in part, because some metallic ions may affix to cationic contaminants instead of the textile. Thus, to achieve a desired level of antimicrobial agent content in the textiles, the textiles may need to be treated with greater amounts of antimicrobial agent when water quality is poor as compared to when water quality is good.

To address problems associated with poor or changed quality water, the washer system 100 can include one or more sensors that measure a quality of water in the system 100 and, based on the measured water quality, dynamically control the amount of antimicrobial agent utilized in a treatment cycle. For example, in the washer system 100 shown in FIG. 1, a first water quality sensor 150A is located in the sixth module 120F and a second water quality sensor 150B is located along the flow line 130. The water quality sensors 150A, 150B may be communicatively coupled to a processor 152. In this way, the water quality sensors 150A, 150B may measure the quality of water in the sixth module 120F and the flow line 130, respectively, and transmit a water-quality signal to the processor 152 indicating the measured water quality. A commercially available example of a water quality sensor is the EXAxt SC450 Conductivity/Resistivity Analyser (Yokogawa North America, Inc., Sugar Land, Tex.). The processor 152 may then process the water-quality signals to determine an amount of antimicrobial agent to be used for a treatment cycles or a plurality of treatment cycles.

Figure 2:
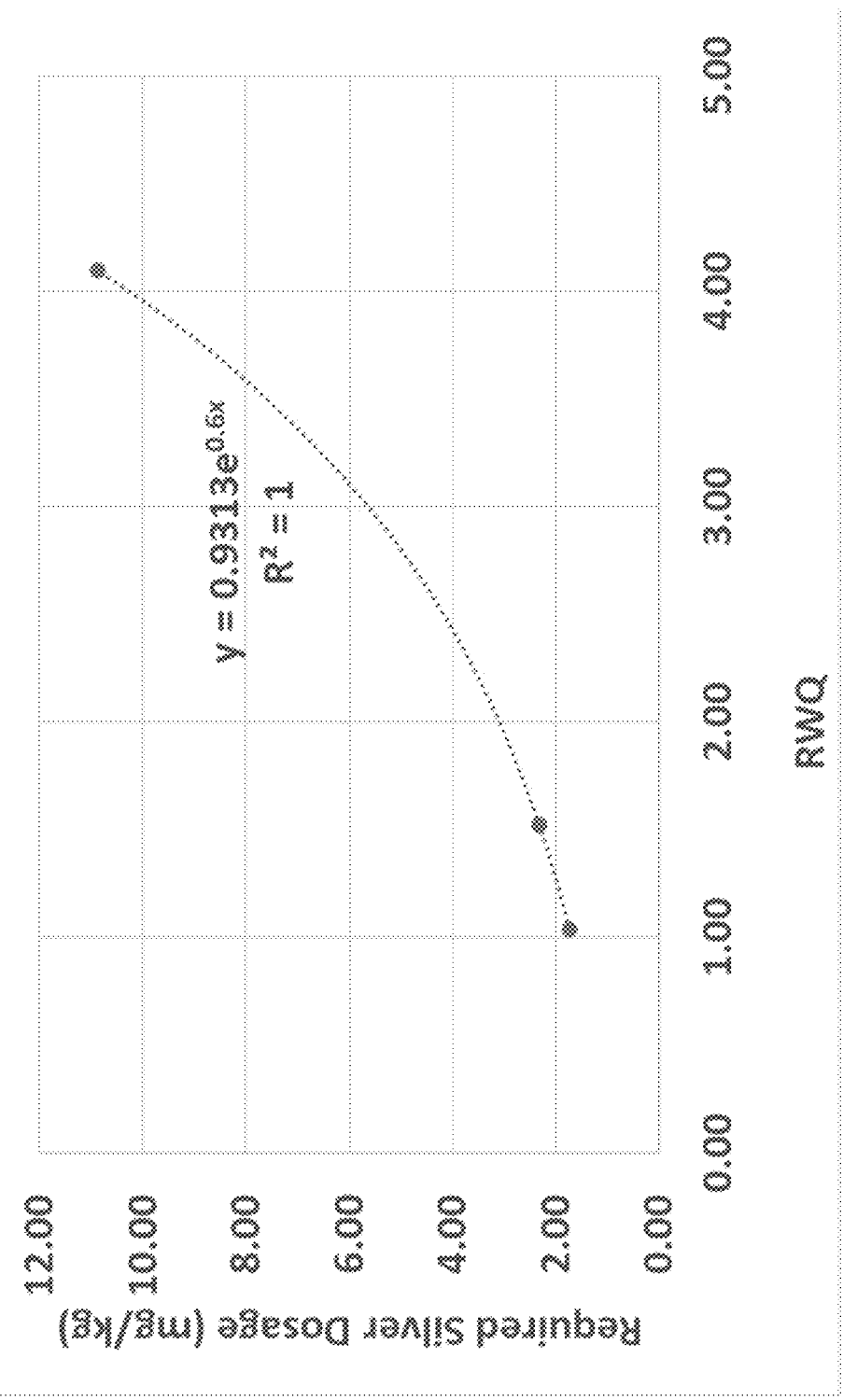
FIG. 2 is a chart illustrating an example model for determining an antimicrobial dosage based on measured water quality according to aspects of the disclosure.

In some examples, the sensors 150A, 150B can measure one or more water quality parameters such as, for instance, a water hardness (e.g., a calcium and/or magnesium concentration), a pH, and/or a total dissolved solids (TDS) concentration. The measured water quality parameters may be weighted and combined by the processor 152 to generate a Relative Water Quality (RWQ) number. In one implementation, a higher RWQ may indicate a higher hardness, TDS level, and/or pH. It has been discovered that as the RWQ increases, an exponentially higher dosage of antimicrobial agent is required to maintain or achieve an efficacious level of antimicrobial agent in the textiles. As such, the processor 152 can be configured to apply one or more algorithms with the RWQ as an input and an antimicrobial dosage as an output. A chart illustrating one example algorithm for determining a dosage of antimicrobial agent (mg antimicrobial agent to Kg textile) based on measured water quality is shown in FIG. 2. It should be understood that other examples are also possible.

In an alternative aspect to address water quality, the system can add polished water to the system prior to the textiles entering the treatment zone. Accordingly prior to the textiles entering the treatment zone, the textiles are subjected to polished water. By the time the textiles enter the treatment zone, water of poor quality associated with the textiles is replaced with polished water, therefore enhancing the effectiveness of the treatment zone.

The processor 152 can be further communicatively coupled to the flow control device 139, which controls the amount of antimicrobial agent that is provided from the antimicrobial agent source 128 to the sixth module 120F. In particular, the processor 152 can provide control signals to the flow control device 139 to cause the flow control device 139 to increase the antimicrobial agent in the sixth module 120F so as to achieve the determined dosage of antimicrobial agent.

To determine an amount of antimicrobial agent to add to the sixth module 120F, the washer system 100 can include a conductivity measurement probe 158 in the sixth module 120F. The conductivity probe 158 can measure a conductivity of the fluid in the sixth module 120F, which can provide an indication of the amount of antimicrobial agent in the fluid. The processor 152 can be communicatively coupled to the conductivity measurement probe 158, receive signals indicating the measured conductivity, determine the amount of antimicrobial agent in the sixth module 120F based on the received signals, and then determine the amount of antimicrobial agent that needs to be added from the antimicrobial agent source 128 to achieve the determined dosage. In one example, the determined dosage can be a dosage that is expected to achieve a target level of efficacy as a result of the treatment cycle.

Although illustrated example includes a water quality sensor 150A in the sixth module 120F and a water quality sensor 150B in the flow line 130, it should be understood that the washer system 100 can include more or fewer water quality sensors in other examples.

The processor 152 may include a general-purpose processor (e.g., a microprocessor) and/or a special-purpose processor (e.g., a digital signal processor (DSP)). The processor 152 may further include a data storage unit having one or more volatile, non-volatile, removable, and/or non-removable storage components, such as magnetic, optical, or flash storage, and/or may be integrated in whole or in part with processor 152. Further, data storage unit may take the form of a non-transitory computer-readable storage medium, having stored thereon program instructions (e.g., compiled or non-compiled program logic and/or machine code) that, when executed by processor 152, cause the washer system 100 to perform one or more acts and/or functions, such as those described in this disclosure. As such, washer system 100 may be configured to perform one or more acts and/or functions, such as those described in this disclosure. Such program instructions may define and/or be part of a discrete software application that can be executed in response to certain inputs being received from a communication interface and/or a user interface, for instance. Data storage unit may also store other types of data, such as those types described in this disclosure.

Although not shown in FIG. 1 for clarity of illustration, the washer system can further include a user interface to facilitate interaction with a user of washer system 100, if applicable. As such, the user interface may include input components such as a keyboard, a keypad, a mouse, a touch-sensitive panel, a microphone, and/or a camera, and/or output components such as a display device (which, for example, may be combined with a touch-sensitive panel), a sound speaker, and/or a haptic feedback system.

Referring now to FIGS. 3-7, example processes are illustrated and described for treating textiles with an antimicrobial agent according to various aspects of the disclosure. It should be understood that, according to alternative aspects of the disclosure, the processes of FIGS. 3-7 can omit steps, include additional steps, and/or modify the order of steps presented above. Additionally, it is contemplated that one or more of the steps presented below can be performed simultaneously. It should also be understood that the example processes of FIGS. 3-7 can correspond to at least some instructions that can be executed by the processor 152 to perform the below described functions.

Figure 3:
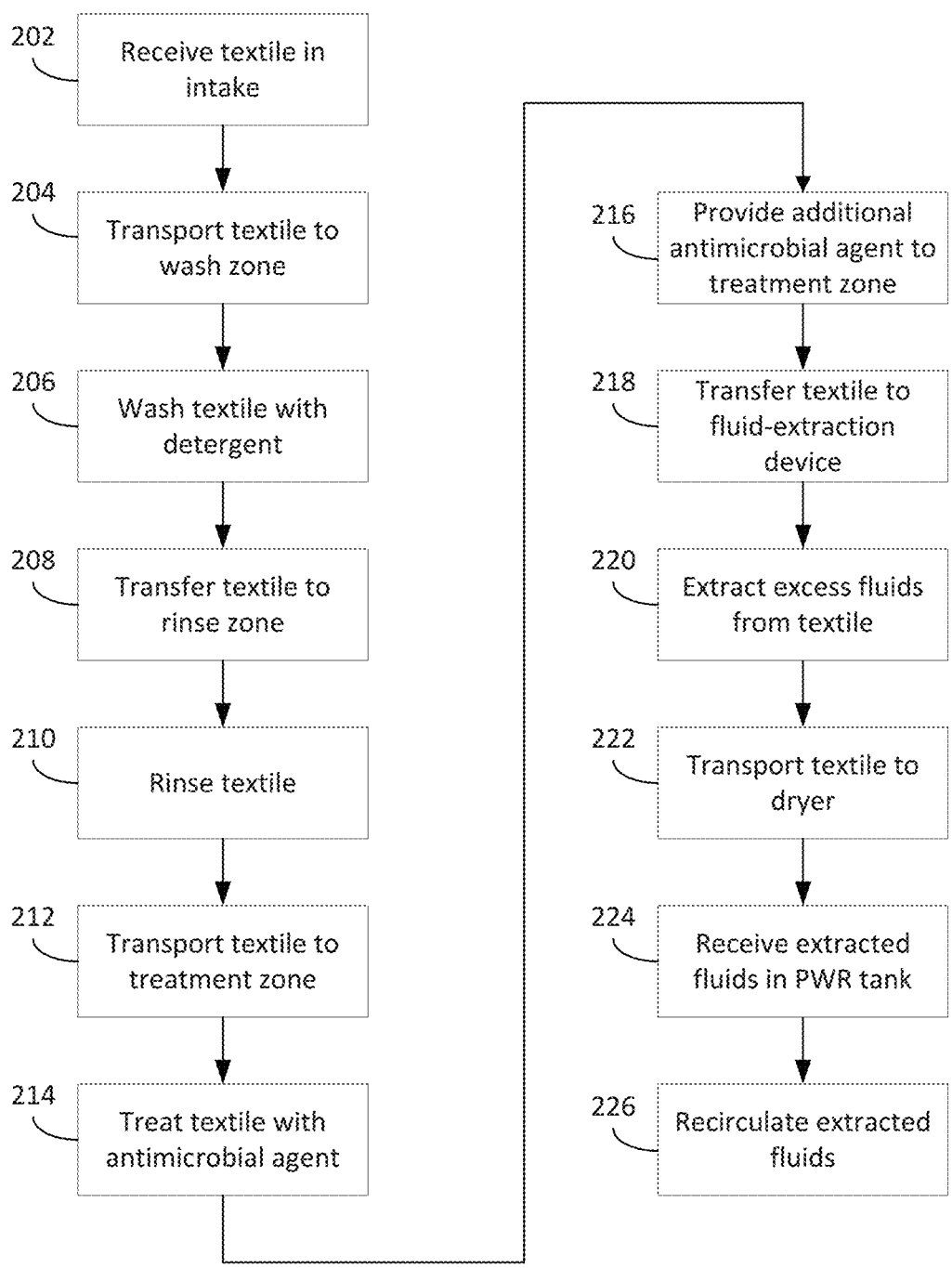
FIG. 3 is a flowchart of an example process for treating textiles with an antimicrobial agent according to aspects of the disclosure.

FIG. 3 illustrates an example flowchart for using a washer system, including a tunnel washer (e.g., the washer system 100), to treat a textile with an antimicrobial agent according to some aspects of the disclosure. At block 202, a textile is received in the intake 114. With the textile in the intake 114, the washer system 100 may provide fluid from the flush tank 142 to the intake 114 to perform a pre-wash cycle on the textile. During the pre-wash cycle, the fluid in the intake 114 may facilitate initial wetting of the textile prior to the main wash zone.

At block 204, the tunnel washer 112 transports the textile from the intake 114 to the wash zone. At block 206, the textile is washed with a detergent and, optionally, other wash chemicals, steam, and/or heat in each of the modules 120A-120C of the wash zone. The detergent can be provided to the wash zone modules 120A-120C from a detergent source 156 as shown in FIG. 1. As the textile is progressed through the modules 120A-120C, the wash fluids counterflow from the third module 120C to the first module 120A (i.e., in the direction of arrow B in FIG. 1), where excess wash fluids are drained via the drain 154.

At block 208, the textile is transferred from the wash zone to the rinse zone. In the example of FIG. 1, the textile is transferred from the third module 120C to the fourth module 120D. At block 210, the textile is rinsed in each of rinse zone modules 120D, 120E with rinse fluids provided by the fresh water source 122, the polished water source 124, and/or the tempered water source 126. Optionally, the textile may additionally or alternatively be rinsed by fluids provided by the PWR tank 138. In particular, the rinse fluids are provided to the last module 120E of the rinse zone so that the rinse fluids counterflow back to the beginning of the rinse zone at module 120D. In this way, the textile may be progressively rinsed in cleaner rinse fluids as it moves through the tunnel washer 112.

At block 212, the textile is transferred from the rinse zone to the treatment zone. In doing so, a portion of the rinse fluids may be transferred with the textile into the treatment zone module 120F. At block 214, the textile is submerged in a treatment solution including the antimicrobial agent. At block 216, the antimicrobial agent source 128 may optionally provide additional antimicrobial agent to the treatment zone module 120F (if necessary) to achieve a treatment solution having a predetermined dosage of antimicrobial agent.

At block 218, the textile is transferred, via the discharge 116, to the fluid-extraction device 118. At block 220, the fluid-extraction device 118 extracts excess fluids from the textile. At block 222, the textile may then be transported to other components for drying and/or finishing (e.g., folding).

In the example washer system 100 described above, the treatment of the textile with antimicrobial agent is described as being performed in a treatment module that is separate from the rinse modules. It should be understood that according to additional or alternative aspects, the treatment functions can be performed in the last rinse module. For example, the treatment may be performed in the last rinse module, which transfers fluids to other modules via counterflow.

At block 224, the PWR tank 138 may receive the extracted fluids from the fluid-extraction device 118. At block 226, the PWR tank 138 may recirculate at least a portion of the extracted fluids back into the tunnel washer 112. For example, the PWR tank 138 may recirculate at least a portion of the extracted fluids back to the fifth module 120E in the rinse zone (or a combined rinse/treatment zone), and/or at to the flush tank 142 for use in the intake 114 as described above.

Figure 4:
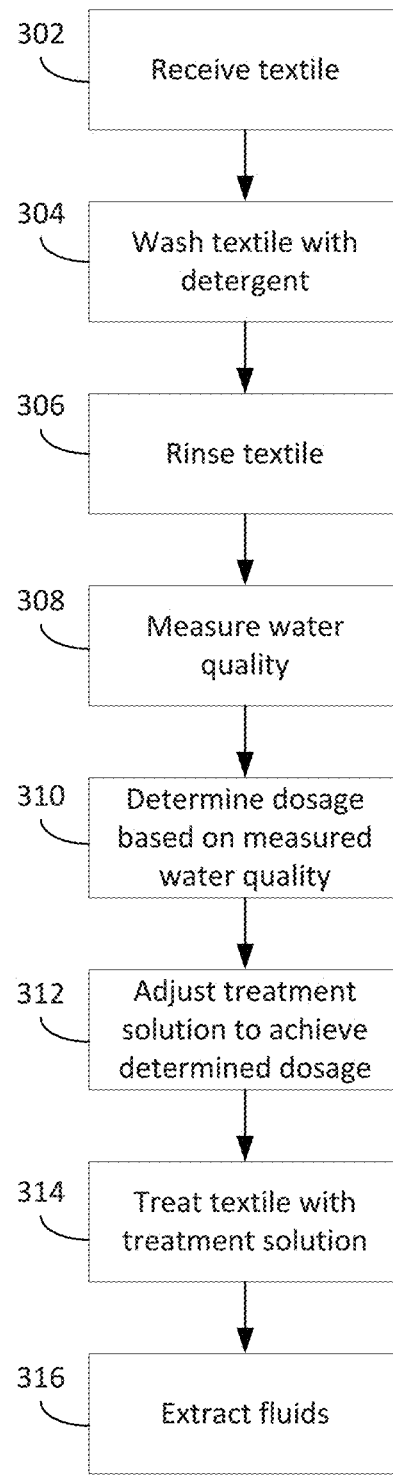
FIG. 4 is a flowchart of another example process for treating textiles with an antimicrobial agent according to aspects of the disclosure.

FIG. 4 illustrates another example flowchart for treating a textile according to additional or alternative aspects of the disclosure. At block 302, the washer system receives a textile to be washed and treated. At block 304, the textile is washed with a detergent during a wash cycle in the washer system. At block 306, the textile is rinsed in the washer system to remove the detergent from the textile. At block 308, one or more sensors measure a quality of water to be used in a treatment cycle. At block 310, a processor determines a dosage of antimicrobial agent to apply to the textile based on the measured quality of water at block 308. At block 312, the washer system adjusts an amount of antimicrobial agent in a treatment solution to achieve the determined dosage. At block 314, the textile is treated with the treatment solution having the determined dosage of antimicrobial agent. At block 316, the washer system extracts excess fluids from the textile.

Aspects of the disclosure are described above in the context of the washer system 100, which includes a tunnel washer 112 having a plurality of modules 120A-120F. However, these aspects of the disclosure can be extended to systems and processes in the context of washer-extraction devices. For example, according to alternative aspects, the one or more water quality sensors can be provided in a washer-extraction device, which may control an amount of antimicrobial agent utilized in a treatment cycle based on water quality measurements.

As noted above, this process can substantially mitigate problems associated with poor and changed water quality used for antimicrobial treatment of textiles. Thus, in some instances, two batches of textiles that are substantially the same may nonetheless be treated with different amounts of antimicrobial agent where the water quality in the washer system is different for each batch.

In some aspects, regardless of the wash system employed, the disclosure is directed to achieving a textile having desired level (i.e., predetermined or target level) of antimicrobial efficacy with a single treatment cycle. In addition, the washer system 100 may be configured to incrementally load the textile with antimicrobial agent to a desired efficacious level over a plurality of treatment cycles. Stated differently, the textile may not achieve a desired, predetermined or target level of antimicrobial efficacy as a result of only a single initial treatment cycle. While an incremental loading approach may require more time than a single cycle approach to initially achieve a textile with a target level of anti-microbial agent that will mitigate microbial infections, it has been found that incremental loading provides substantial cost savings and ecological benefits over the useful life of the textile as compared to the single cycle approach.

In single cycle approaches, treatment solutions may contain a concentration of approximately 2 parts per million (PPM) to about 100 PPM. Although such high concentrations of antimicrobial agent may be beneficial for an initial treatment cycle, the same concentrations provide substantially diminished benefits with each successive treatment cycle on the same pieces textile. In particular, once a certain level of antimicrobial agent content or uniformity is achieved in the textile, further increases in antimicrobial agent content may provide negligible (if any) additional benefit. Therefore, repeated treatment cycles involving a moderate dose of an antimicrobial agent can achieve the same antimicrobial efficacy as repeated cycles involving high doses of agent, albeit it may take more than one moderate dose cycle to achieve the desired efficacy.

In contrast to single cycle antimicrobial treatment approaches, the incremental-loading-to-efficacy approach of the disclosure utilizes substantially less antimicrobial agent during each treatment cycle. For example, according to some examples, the concentration of the antimicrobial agent in the treatment solution can be approximately 3 PPM to approximately 8 PPM. Accordingly, the more times a textile is treated using the incremental-loading-to-efficacy approach, the greater the cost savings realized as compared to approaches using dosing concentrations that may achieve a desired anti-microbial efficacy in a single treatment. Moreover, by reducing the amount of antimicrobial agent used per treatment cycle, less antimicrobial agent is likely to be drained to waste.

In some examples, the predetermined efficacious level can be approximately 0.6 mg of antimicrobial agent per kg of textile. In other examples, the predetermined efficacious level can be approximately 0.75 mg of antimicrobial agent (e.g., silver ion) per kg of textile. In still other examples, the predetermined efficacious level can be approximately 1.3 mg antimicrobial agent per 1 Kg textile, approximately 1.5 mg antimicrobial agent per 1 Kg textile, approximately 1.7 mg antimicrobial agent per 1 Kg textile, approximately 2 mg antimicrobial agent per 1 Kg textile, approximately 3 mg antimicrobial agent per 1 Kg textile, or approximately 4 mg antimicrobial agent per 1 Kg textile.

In some examples, the amount of antimicrobial agent utilized per treatment cycle can be determined to facilitate maintaining a textile at or above the desired, predetermined, or target efficacious level. When previously treated textiles are washed and rinsed the washer system 100, some antimicrobial agent previously contained within the textile washes out. Accordingly, in some examples, the amount of antimicrobial agent employed per treatment cycle may be less than an amount required to achieve a target efficacy after a single laundry cycle and greater than or equal to an amount required to replace the antimicrobial agent that is expected to leach from the textile during laundry cycles after efficacy is achieved. In one example implementations, the amount of antimicrobial agent utilized per treatment cycle is selected such that the textile maintains a content level of approximately 1 mg of antimicrobial agent per kg of textile to approximately 15 mg of antimicrobial agent per kg of textile, for instance 1, 2, 3, 4, 5, 6, 7, 8, 9, 10, 11, 12, 13, 14 or mg/Kg. In another example implementation, the amount of antimicrobial agent utilized per treatment cycle is selected such that the textile maintains a content level of approximately 5 mg of antimicrobial agent per kg of textile to approximately 10 mg of antimicrobial agent per kg of textile.

Depending on the type of textile being laundered, the concentration of the antimicrobial agent in the treatment cycle can be about 0.5 mg of antimicrobial agent per kg of textile to about 30 mg of antimicrobial agent per kg of textile. For example, the concentration of the antimicrobial agent in the treatment cycle can be approximately 20% to approximately 90% lower than the dosage values shown in Table 1. In other examples, the concentration of the antimicrobial agent in the treatment cycle can be such that the textile achieves a content level of about 0.2 mg/kg, about 0.3 mg/kg, about 0.4 mg/kg, about 0.5 mg/kg, about 0.6 mg/kg, about 0.7 mg/kg, or about 0.8 mg/kg after the first treatment cycle. At such concentrations, multiple laundry/treatment cycles may be required to achieve the predetermined level of antimicrobial agent in the textile. In some embodiments, a desired level of the antimicrobial agent in the textile (e.g., between about 1.0 mg/kg to about 2.0 mg/kg) can be achieved in a single treatment cycle.

In various embodiments, newly manufactured textiles or previously untreated laundry is treated in a first treatment cycle that infuses the textile with less than 1 mg antimicrobial agent per kilogram of textile. Repeated treatment cycles on the laundry raises the antimicrobial agent in the textiles from about 1 mg/Kg to about 5 mg/Kg of antimicrobial agent per kilogram of textile.

In some examples, the amount of antimicrobial agent utilized per treatment cycle can be determined so that the predetermined efficacious level is achieved only after a predetermined number of treatment cycles. For instance, the predetermined number of treatment cycles can be two treatment cycles, three treatment cycles, four treatment cycles, five treatment cycles, 10 treatment cycles, or 30 treatment cycles according to various examples. Other examples are also possible.

As noted above, the amount of antimicrobial agent in the textile may continue to increase or reach a steady state with each successive treatment cycle when existing antimicrobial treatment approaches are employed. In such approaches, the textiles may become discolored when loaded with too much antimicrobial agent (e.g., greater than 100 mg/kg of textile). Accordingly, a further benefit to the incremental-loading-to-efficacy approach is that the textiles can be treated a substantially greater number of times without causing distortion in color in the textile. For example, in some instances, textiles can be treated more than 30 times, more than 50 times, or more than 100 times without causing distortion in color to the textiles when the incremental-loading-to-efficacy approach of the disclosure is employed.

Figure 5:
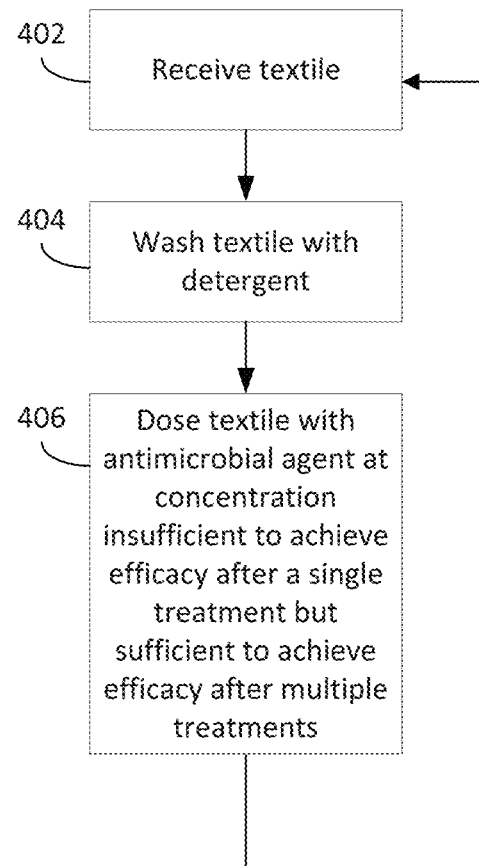
FIG. 5 is a flowchart of yet another example process for treating textiles with an antimicrobial agent according to aspects of the disclosure.

Referring now to FIG. 5, an example flowchart for treating a textile with an antimicrobial agent over a plurality of laundry cycles is illustrated according to some aspects of the disclosure. At block 402, the washer system receives the textile for a laundry cycle. At block 404, the washer system washes the textile with a detergent. At block 406, the washer system doses the textile with a solution having a predetermined concentration of an antimicrobial agent. The process is then repeated for a plurality of additional laundry cycles. The predetermined concentration is insufficient to achieve a predetermined antimicrobial efficacy for the textile due to the first laundry cycle alone (i.e., due to the first iteration of blocks 402-406) but sufficient to achieve the predetermined antimicrobial efficacy for the textile due to a combination of the first laundry cycle and one or more of the plurality of additional laundry cycles.

In some examples, the process can include providing the textile to a customer and then receiving the textile back from the customer between each laundry cycle. In other examples, the process may further include providing the textile to a customer only after the textile achieves the predetermined antimicrobial efficacy (e.g., after multiple laundry cycle(s)).

According to still further aspects of the disclosure, a process for protecting a laundry supply chain is provided. It is known that healthcare associated infections are a growing concern with some pathogens being virtually untreatable with conventional methods. With such healthcare associated infections, the harmful microbes are often carried in the linens and clothing used within a hospital. Conventional laundry methods are known to be unreliable to effectively disinfect or sanitize laundry. Even so if such methods were effective, once hospital textiles have been laundered and treated, they are susceptible to recontamination. Pathogens carried by these textiles can infect hospital patients and even cause death. Since most hospital patients spend the majority of their time between the sheets of a hospital bed or in a hospital gown, hospital linens are the core of the overall hospital environment for the patient, and a primary site in the battle against infection. To combat such infections, and to protect not only patients, but healthcare workers and anyone in contact with hospital laundry (including laundry staff), the loading of an antimicrobial agent into an inventory of a laundry from a healthcare facility can protect the complete supply chain for such inventory. Not only does the antimicrobial agent kill pathogens in soiled laundry during the laundry process, the agent infused into the textiles protects the textiles against new pathogens that come in contact with the textiles. This treatment may also act as textile preservative, protecting the textiles from storage based microbial and fungal growth.

Figure 6:
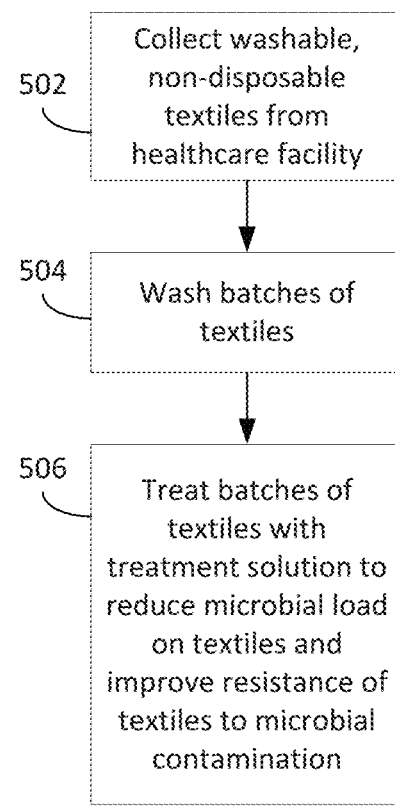
FIG. 6 is a flowchart of a further example process for treating textiles with an antimicrobial agent according to aspects of the disclosure.

Referring now to FIG. 6, an example flowchart for protecting individuals in contact with healthcare facility linens from a healthcare associated infection is illustrated according to some aspects. At block 502, substantially all washable, non-disposable textiles that contact patients and healthcare workers are collected in one or more batches at a healthcare facility. At block 504, each batch is washed using a washer system (e.g., the washer system 100) using a detergent. At block 506, each batch is treated with a treatment solution including a predetermined concentration of an antimicrobial agent to reduce the microbial load on the textiles in the batch and improve a resistance of the textiles in the batch to microbial contamination responsible for healthcare associated infections. By treating substantially all washable, non-disposable textiles at a healthcare facility, healthcare associated infections may be reduced. In addition, microbial discharge to the environment may be reduced.

Figure 7:
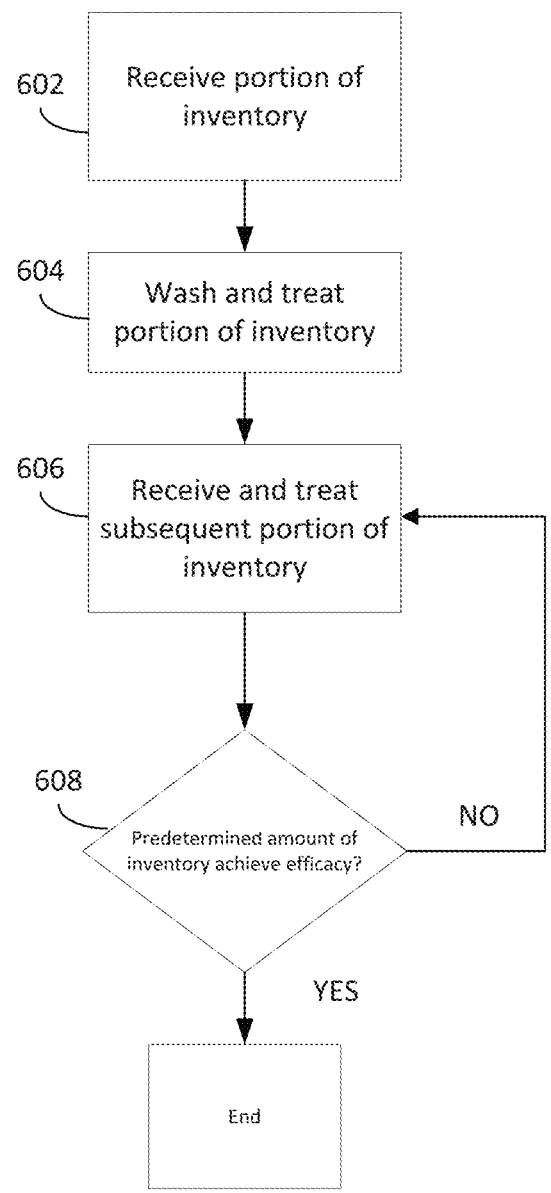
FIG. 7 is a flowchart of another example process for treating textiles with an antimicrobial agent according to aspects of the disclosure.

Referring to FIG. 7, another example flowchart for reducing a microbial load in an inventory of textiles including a plurality of pieces at a healthcare facility is illustrated according to some aspects. At block 602, the washer system receives a first portion of the plurality of pieces of the inventory in a wash basin of the washer system for a laundry cycle. At block 604, the washer system initiates the laundry cycle. The laundry cycle includes a wash cycle and a treatment cycle. The treatment cycle includes a solution having a predetermined concentration of an antimicrobial agent. At block 606, the washer system receives and treats a subsequent portion of the inventory. At block 608, it is determined whether a predetermined amount of the pieces of the inventory have achieved a predetermined efficacy, thereby reducing the antimicrobial load of the entire inventory. In one example, the predetermined amount of pieces is approximately 50%-90% of the inventory, for example, 50%, 60%, 70%, 80% or 90% of the inventory.

In order to determine whether textiles have been subject to the antimicrobial treatments as described herein, an additional aspect of the disclosure is a method of detecting the presence of an efficacious amount of silver in a textile. The method uses two solutions, a first solution and a second solution. The first solution includes the following reagents: Cadion 2B (CAS No. 6708-61-8), a buffer sufficient to maintain a pH in the range of from about 8 to about 10, and a surfactant. The second solution includes Cadion 2B, a buffer sufficient to maintain a pH in the range of from about 8 to about 10, a surfactant, and a complexing agent. The method relies upon the formation of a complex of the complexing agent and silver, wherein the formation of the agent/silver complex is more favorable than formation of a complex of Cadion 2B and silver. As part of the method, the solutions are dispensed on to separate areas of the textile and the color of the dispensed first solution is compared to the color of the dispensed second solution.

Solution A in contacted with a silver-impregnated textile results in a visible color change of the solution due to the formation of a red-violet complex of Cadion 2B and silver, while contacting Solution B with a silver-impregnated textile does not result in a visible color change of the solution due to favorable formation of a complex of the complexing agent and silver. In some aspects, a difference in the color of Solution A and Solution B after dispensation onto a textile indicates an efficacious of silver.

In some aspects, the amount of Cadion 2B included in Solution A or Solution B is any amount in which a change in the color of the solution is visible upon exposure to silver. In some embodiments, Solution A or Solution B may contain Cadion 2B in a range of about 0.001 wt % to about 0.005 wt %, or about 0.002 wt % to about 0.004 wt %, or about 0.002 wt %, or about 0.003 wt %, or about 0.004 wt %.

In some embodiments, Solution A or Solution B may further comprise a masking agent to react with chemical species that may interfere with the detection of silver. In some embodiments, the masking agent is ethylenediaminetetraacetic acid (EDTA), cyclohexanediaminetetraacetic acid (CDTA), diethylenetriaminepentaacetic acid (DTPA), nitrilotriacetic acid (NTA), or N-(hydroxyethyl)-ethylenediaminetriacetic acid (HEDTA). In some aspects, Solution A or Solution B may contain the masking agent in a range of about 0.5 wt % to about 1.6 wt %, or about 0.9 wt % to about 1.2 wt %, or about 0.9 wt %, or about 1.0 wt %, or about 1.1 wt %.

In some embodiments, Solution A or Solution B may further comprise a water-miscible organic solvent. In some aspects, the water-miscible organic solvent may function as a solubilizer. In some embodiments, the water-miscible organic solvent is N-methyl-2-pyrrolidone, polyethylene glycol 400 (PEG400), N,N-dimethylacetamide (DMA), or dimethylsulfoxide (DMSO). In some aspects, Solution A or Solution B may contain the water-miscible solvent in a range of about 2.5 vol % to about 3.2 vol %, or about 2.7 vol % to about 3.0 vol %, or about 2.7 vol %, or about 2.8 vol %, or about 2.9 vol %, or about 3.0 vol %.

In some aspects, the complexing agent may be any compound for which the formation of a complex of the compound and silver is more favorable than formation of a complex of Cadion 2B and silver. In some embodiments, the complexing agent is thiosulfate, ammonia, or cyanide. In some aspects, Solution B may contain the complexing agent in a range of about 0.3 wt % to about 0.9 wt %, or about 0.5 wt % to about 0.7 wt %, or about 0.5 wt %, or about 0.6 wt %, or about 0.7 wt %.

In some aspects, the surfactant of Solution A or Solution B may be any non-ionic surfactant. In some embodiments, the surfactant of Solution A or Solution B is TWEEN® 20, TWEEN® 80, TRITON™ X-100, n-dodecyl β-D-maltoside (DDM), digitonin, sarkosyl, or sodium dodecyl sulfate (SDS). In some aspects, Solution A or Solution B may contain the surfactant in a range of about 0.5 vol % to about 1.4 vol %, or about 0.75 vol % to about 1.15 vol %, or about 0.8 vol %, or about 0.9 vol %, or about 1.0 vol %, or about 1.1 vol %.

In some aspects, the buffer of Solution A or Solution B may be any buffer sufficient to maintain a pH in the range of from about 8 to about 10. In some embodiments, the buffer may comprise one or more of potassium tetraborate, sodium borate, citric acid, sodium citrate, hydrochloric acid, sodium hydroxide, sodium carbonate, sodium bicarbonate, monosodium phosphate, monopotassium phosphate, dipotassium phosphate, or potassium chloride.

EXAMPLES

Example 1: Silver Treatment of Hospital Textiles

A system for the application of silver ions to textiles as described herein (SILVACLEAN® system from Applied Silver, Hayward, Calif.) was installed at a Healthcare Laundry Accreditation Council (HLAC) accredited laundry facility serving three different hospitals. Following a wash cycle, sheets and patient gowns were allowed to soak for approximately two minutes in a bath containing silver at a concentration between 1.7 and 1.8 mg Ag per liter of wash liquor (i.e., about 1.7-1.8 ppm) before the textiles were extracted and dried. Textiles were dosed to contain between 1.3 and 15 mg Ag per kilogram (e.g., between 8 and 10 mg Ag per kilogram). The textiles were analyzed daily via inductively coupled plasma-atomic emission spectrometry (ICP-AES) to ensure treatment within target range.

Example 2: Reduction of Microbial Bioburden of Hospital Textiles

Sheets and gowns, which were selected over other types of hospital textiles because they have easily identifiable patient-facing surfaces, were sampled before and after patient use (referred to as pre- and post-patient use, respectively). Pre-patient use samples were randomly selected from clean linen storage carts in multiple hospital wards, which were selected based on hospital layout and sampling logistics. A set of gowns and sheets were selected each day using a random number generator to select ward, cart, stack within the cart, and item within the stack. Pre-patient use samples were handled with clean nitrile gloves and placed in clean plastic bags for transport to the sampling room where microbiologic samples were collected.

Post-patient use samples were sampled after patient discharge, following patient transfer, or after routine bed linen and gown changes. Microbiologic sampling was carried out immediately after discharge, before beds were stripped and cleaned by the housekeeping staff. The hospital directed patients to leave gowns open on the bed so that both the fitted bottom sheet and gown could be sampled without directly handling the item. Used textiles in each hospital were sampled for approximately 10 days between the hours of 9 a.m. and 5 p.m.

Two samples were collected from each textile item at pre-defined, patient-facing locations. On bottom fitted sheets, samples were taken in the center middle of the sheet, both upper and lower, roughly corresponding to a supine patient's mid and lower back. On gowns, one sample was taken in the center chest area and another in the center of the suprapubic region. If the target sample area was visibly soiled, the sample was taken on the same sheet or gown, but in a directly adjacent unsoiled area.

Samples were collected using three types of culture media: non-selective Tryptic Soy Agar (TSA) was used for total aerobic colony count, S. aureus selective Baird-Parker Agar to quantify S. aureus, and MRSA selective HARDYCHROM™ MRSA media (all Hardy Diagnostics, Santa Maria, Calif.). Plates had a surface area of 28.27 cm$^2$. A random number generator was used to assign textiles to specific sampling media, ensuring approximately 20% of total samples would be on selective media (10% S. aureus and 10% MRSA). Contact plate sampling was carried out using the instructions for use provided by the manufacturer. The plate was held in place for five seconds, lifted from the sheet, and then immediately re-capped. Contact plates were incubated for 24 hours in aerobic conditions at 37° C. and total colony forming units (CFU) per plate were then enumerated by an independent lab. If the colony counts were greater than 300, the count was recorded as 300 CFU/plate. This was done to limit the effect of outliers and because plates with more than 300 CFU/plate could not be counted reliably.

The average of two sampling sites per textile was calculated, resulting in a single measure for each gown and sheet. The Wilcoxon rank-sum test was used to compare means in each group and Fisher's exact test was used to compare the proportions of textiles from which bacterial colonies were isolated. To control for the three different hospital sites and ward types, mixed-effects logistic models were constructed to study the association between silver treatment and the isolation of bacteria for each culture media used (non-selective, S. aureus, and MRSA). For all models, the dependent variable was the isolation of bacteria on the specific media type. The independent variables included were presence or absence of silver treatment, if the textile was pre or post-patient use, and the ward where the samples had been collected. Wards were simplified to two levels: non-monitored wards (which included non-critical medical/surgical floors, labor and delivery, acute rehabilitation, and non-monitored pediatric beds) and more critical care oriented monitored wards (including telemetry wards, intensive care units, and cardiac care units). First, mixed-effects models that consisted of a single independent variable controlling for hospital clustering as a random effect were constructed. A multivariate mixed-effects logistic model was then constructed, using information-theoretic model selection to generate all possible combinations of the selected independent variables. The model with the lowest corrected Akaike information criterion was selected (See, Burnham & Anderson, "Model selection and multimodel inference: a practical information-theoretic approach," $2^{nd}$ ed., New York: Springer Verlag (2002)). Multicollinearity between independent variables in multivariate models was assessed using variance inflation factors.

Analysis was conducted in R (R Core Team, 2015) utilizing the lme4 package (Bates et al., 2015) for logistic mixed effects models and the MuMIn package for information-theoretic model selection (Bartoń, 2015). (R Core Team, 2015: R: A language and environment for statistical computing. R Foundation for Statistical Computing, Vienna, Austria. Bates, D., Maechler, M., Bolker, B., Walker, S., 2015: lme4: Linear mixed-effects models using Eigen and S4. R package version 1.1-9. Bartoń, K., 2015: MuMIn: Multi-Model Inference. R package version 1.15.1.)

A total of 1,912 gowns and 2,074 sheets were included in the analysis. Fifty-nine percent of the gown samples (1,133/1,912) and 51% percent of the sheet samples (1,059/2,074) were collected pre-patient use. *Staphylococcus aureus* specific cultures were obtained on 9.5% of gowns (181/1912) and 8.3% of sheets (173/2074). MRSA specific cultures were obtained on 10% of gowns (193/1912) and 9% of sheets (187/2074).

Example 3: Aerobic Bacterial Colony Isolation Before and after Silver Application More bacteria were isolated from textiles that had been used by patients. Before silver application, 8 times more aerobic bacterial colonies were isolated on non-selective media from post-patient use gowns compared to pre-patient use (113.2+6.4 CFU/plate compared to 14+0.6 CFU/plate, p<0.0001), and slightly more than 10 times more aerobic bacterial colonies were isolated from sheets post-patient use compared to pre-patient use sheets (54.8+3.2 CFU/plate compared to 5.2+0.5 CFU/plate, p<0.0001).

Figure 8:
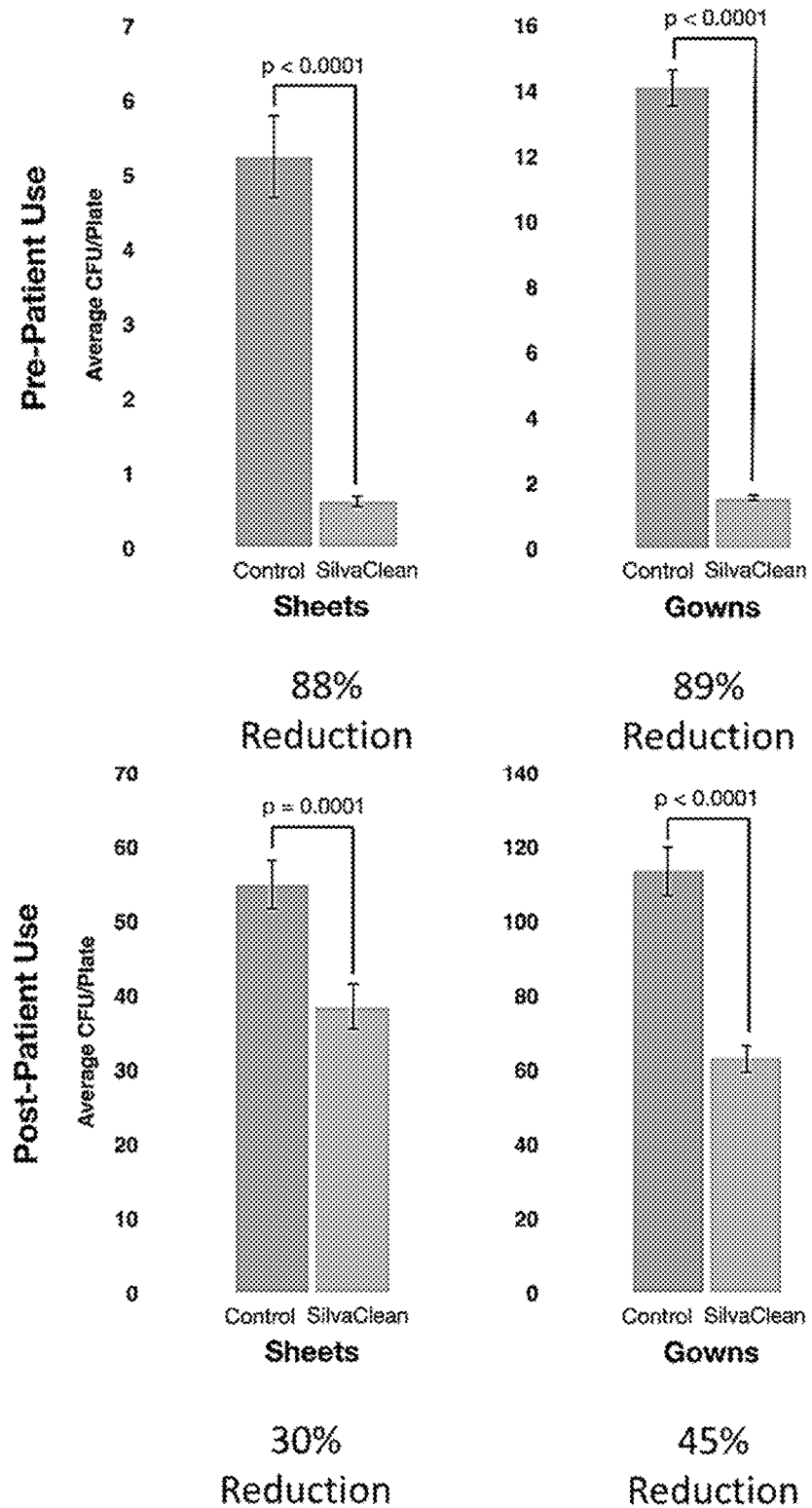
FIG. 8 shows the average CFU/plate for aerobic bacterial colonies before (control) and after silver application. Plates had a surface area of 28.27 cm$^2$.

Fewer total aerobic bacterial colonies were isolated on non-selective culture media on textiles treated with silver (See, FIG. 8). On pre-patient use gowns, an average of 14+0.6 CFU/plate were isolated before silver treatment compared to an average of 1.5+0.07 CFU/plate in the silver treated group, representing an 89% reduction (p<0.0001). Before silver treatment, an average of 5.2+0.5 CFU/plate were isolated from pre-patient use sheets compared to an average of 0.6+0.06 CFU/plate in the silver treated group, representing an 88% reduction (p<0.0001). In gowns sampled after patient use, there was a 45% reduction in bacteria isolated on the silver treated gowns compared to gowns sampled before silver treatment (113.2+6.4 CFU/plate before silver treatment compared to 62.7+3.6 CFU/plate, p<0.0001). In sheets sampled after patient use, there was a 30% reduction in bacteria isolated, with an average of 54.8+3.2 CFU/plate before silver treatment compared to an average of 38.3+2.9 CFU/plate after silver treatment (p=0.0001).

The proportion of pre-patient use gowns from which at least one aerobic bacterial colony was isolated (See, Table 2) fell from 93% (432/466) to 72% (330/459) after silver treatment (Fisher's exact test, p<0.0001). In post-patient use gowns, the proportion fell from 98% (303/310) to 93% (281/303) after silver treatment (p=0.0002). The proportion of sheets with at least one aerobic bacterial colony decreased from 89% (406/454) to 50% (230/457) after silver treatment (p<0.0001) in the pre-patient use group and from 99% (406/409) to 94% (372/394) in the post-patient use group (p<0.0001).

TABLE 2

Proportion of Textiles with Bacterial Isolates Before (Control) and After Silver Treatment

| Textile Type | Culture Media | Group | Isolated, n(%) | None Isolated, n(%) | p Value* |
|---|---|---|---|---|---|
| Pre-Use Gowns | All aerobic | Control | 432 (93%) | 34 (7%) | — |
| | | Silver | 330 (72%) | 129 (28%) | <0.0001 |
| | S. aureus | Control | 28 (53%) | 25 (47%) | — |
| | | Silver | 0 (0%) | 45 (100%) | <0.0001 |
| | MRSA | Control | 18 (29%) | 45 (71%) | — |
| | | Silver | 1 (2%) | 46 (98%) | 0.0002 |
| Post-Use Gowns | All aerobic | Control | 303 (98%) | 7 (2%) | — |
| | | Silver | 281 (93%) | 22 (7%) | 0.003 |
| | S. aureus | Control | 29 (83%) | 6 (17%) | — |
| | | Silver | 23 (48%) | 25 (52%) | 0.001 |
| | MRSA | Control | 9 (26%) | 25 (74%) | — |
| | | Silver | 0 (0%) | 49 (100%) | 0.0001 |
| Pre-Use Sheets | All aerobic | Control | 406 (89%) | 48 (11%) | — |
| | | Silver | 230 (50%) | 227 (50%) | <0.0001 |
| | S. aureus | Control | 5 (23%) | 17 (77%) | — |
| | | Silver | 0 (0%) | 46 (100%) | 0.002 |
| | MRSA | Control | 2 (6%) | 31 (94%) | — |
| | | Silver | 0 (0%) | 47 (100%) | 0.16 |
| Post-Use Sheets | All aerobic | Control | 406 (99%) | 3 (1%) | — |
| | | Silver | 372 (94%) | 22 (6%) | <0.0001 |
| | S. aureus | Control | 38 (84%) | 7 (16%) | — |
| | | Silver | 32 (53%) | 28 (47%) | 0.0008 |
| | MRSA | Control | 9 (21%) | 34 (79%) | — |
| | | Silver | 7 (11%) | 57 (89%) | 0.17 |

*Fisher's exact test, significance considered to be <0.05

In an unadjusted mixed-effects logistic model controlling only for hospital site clustering (See, Table 3), the presence of silver was associated with decreased isolation of aerobic bacteria on non-selective media (odds ratio [OR] 0.1, 95% Confidence Interval [CI] 0.1-0.2). In the best-fit multivariable mixed-effects logistic model for isolation of aerobic bacterial colonies on non-selective media, isolation of colonies was more likely on post-patient use textiles (adjusted OR 9.5, 95% CI 7.1-13) and gowns (adjusted OR 1.5, 95% CI 1.5-2.3) and less likely after silver treatment (adjusted OR 0.1, 95% CI 0.1-0.2). While textiles in critical care areas appeared to be more likely to have colonies isolated in the initial unadjusted model, this variable did not improve model fit in the fully adjusted model, suggesting confounding from other independent variables explained the initial finding.

TABLE 3

Unadjusted and Adjusted Mixed-Effects Logistic Models

| | | All Aerobic | |
| --- | --- | --- | --- |
| | %(n) | Unadjusted (OR, 95% CI) | Adjusted (OR, 95% CI) |
| Ward Type | | | |
| Non-Monitored | 83% (2191) | Ref | — |
| Monitored | 95% (569) | 4.1 (2.8-6.1)* | — |
| Patient Exposure | | | |
| Pre-Use | 76% (1298) | Ref | Ref |
| Post-Use | 96% (1362) | 7.9 (5.9-10.6)* | 9.5 (7.1-13.0)* |
| Textile Type | | | |
| Sheet | 82% (1414) | Ref | Ref |
| Gown | 87% (1346) | 1.5 (1.2-1.8)* | 1.8 (1.5-2.3)* |
| Silver Treatment | | | |
| Absent | 94% (1547) | Ref | Ref |
| Present | 75% (1213) | 0.1 (0.1-0.2)* | 0.1 (0.1-0.2)* |

Abbreviations:
OR, Odds ratio;
CI, Confidence Interval;
*p < 0.05

The proportion of pre-patient use sheets deemed hygienically clean (<20 CFU/dm$^2$, TRSA Standard for Producing Hygienically Clean Reusable Textiles for Use in the Healthcare Industry) increased from 74% (334/454) to 99% (453/457) after silver treatment. The proportion of pre-patient use gowns deemed hygienically clean increased from 30% (139/466) to 98% (448/459) after silver treatment. Results are summarized in Table 4.

TABLE 4

Hygienically Clean Test, Non-Selective Culture Media

| Textile Type | Group | Pass, n (%) | Fail, n (%) |
| --- | --- | --- | --- |
| Pre-Use Sheets | Control | 334 (74%) | 120 (36%) |
| | Silver | 453 (99%) | 4 (1%) |
| Pre-Use Gowns | Control | 139 (30%) | 327 (70%) |
| | Silver | 448 (98%) | 11 (2%) |

Example 4: *S. aureus* Isolation Before and after Silver Application

Figure 9:
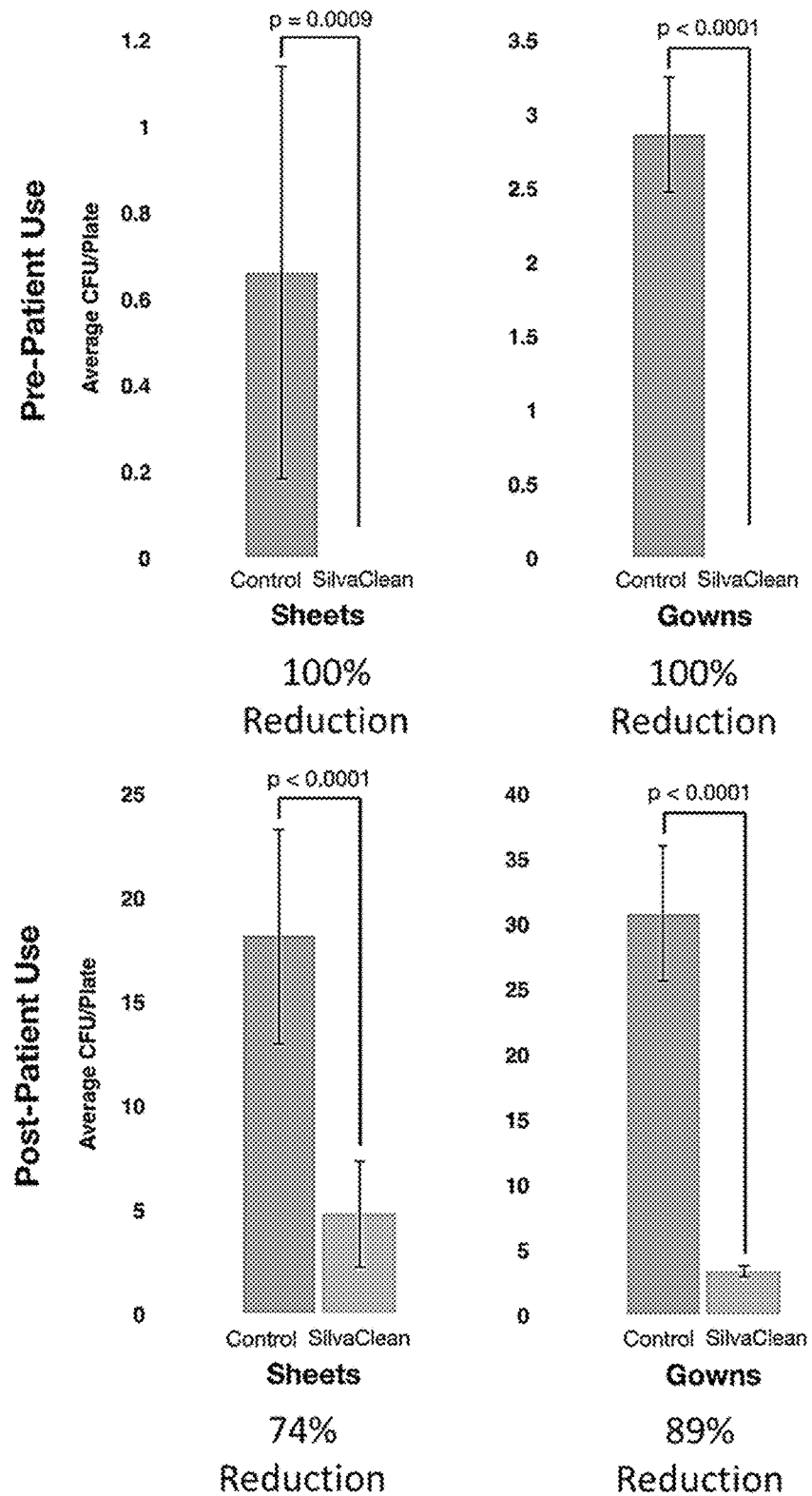
FIG. 9 shows the average CFU/plate for *S. aureus* colonies before (control) and after silver application. Plates had a surface area of 28.27 cm$^2$.

Fewer *Staphylococcus aureus* colonies were isolated on textiles sampled after silver treatment (See, FIG. 9). There was a 100% reduction in *S. aureus* in gowns (2.8+0.3 CFU/plate compared to no *S. aureus* isolated after silver treatment, p<0.0001) and sheets prior to patient use (0.6+0.4 CFU/plate compared to no *S. aureus* isolated after silver treatment, p=0.009). In post-patient use gowns there was a 89% reduction in *S. aureus* colonies isolated, with an average of 30.7+5.1 CFU/plate isolated before silver treatment and 3.3+0.4 CFU/plate after treatment (p<0.0001). There was a 74% reduction in the average number of *S. aureus* colonies isolated from sheets after patient use, with 18.1+5.1 CFU/plate isolated before silver treatment compared to 4.7+2.5 CFU/plate in the silver treated sheets (p<0.0001).

The proportion of pre-patient use gowns from which at least one colony of *S. aureus* was isolated (See, Table 2) fell from 53% (28/53) to 0% (0/45) after silver treatment (Fisher's exact test, p<0.0001). In post-patient use gowns, the proportion fell from 83% (29/35) to 48% (23/48) after silver treatment (p=0.001). The proportion of sheets with at least one colony of *S. aureus* decreased from 23% (5/22) to 0% (0/46) after silver treatment (p=0.002) in the pre-patient use group and from 84% (38/45) to 53% (32/60) in the post-patient use group (p=0.0008).

In an unadjusted mixed-effects logistic model controlling only for hospital site clustering (See, Table 5), the presence of silver was associated with decreased isolation of *S. aureus* colonies (OR 0.2, 95% CI 0.1-0.3). In the best-fit multivariable mixed-effects logistic model for isolation of *S. aureus*, isolation of bacteria was more likely on post-patient use textiles (adjusted OR 11.9, 95% CI 6.1-23.4) and textiles in intensive care settings (adjusted OR 3.9, 95% CI 2.1-7.8) and less likely after silver treatment (adjusted OR 0.1, 95% CI 0.05-0.2).

TABLE 5

Unadjusted and Adjusted Mixed-Effects Logistic Models

| | | *S. aureus* Specific Media | |
| --- | --- | --- | --- |
| | %(n) | Unadjusted (OR, 95% CI) | Adjusted (OR, 95% CI) |
| Ward Type | | | |
| Non-Monitored | 34% (94) | Ref | Ref |
| Monitored | 79% (61) | 7.2 (3.9-13.3)* | 3.9 (2.1-7.8)* |
| Patient Exposure | | | |
| Pre-Use | 20% (33) | Ref | Ref |
| Post-Use | 65% (122) | 9.7 (5.7-16.7)* | 11.9 (6.1-23.4)* |
| Textile Type | | | |
| Sheet | 43% (75) | Ref | — |
| Gown | 44% (80) | 0.9 (0.6-1.4) | — |
| Silver Treatment | | | |
| Absent | 64% (100) | Ref | Ref |
| Present | 27% (55) | 0.2 (0.1-0.3)* | 0.1 (0.05-0.2)* |

Abbreviations:
OR, Odds ratio;
CI, Confidence Interval;
*p < 0.05

Example 5: MRSA Isolation Before and after Silver Application

Figure 10:
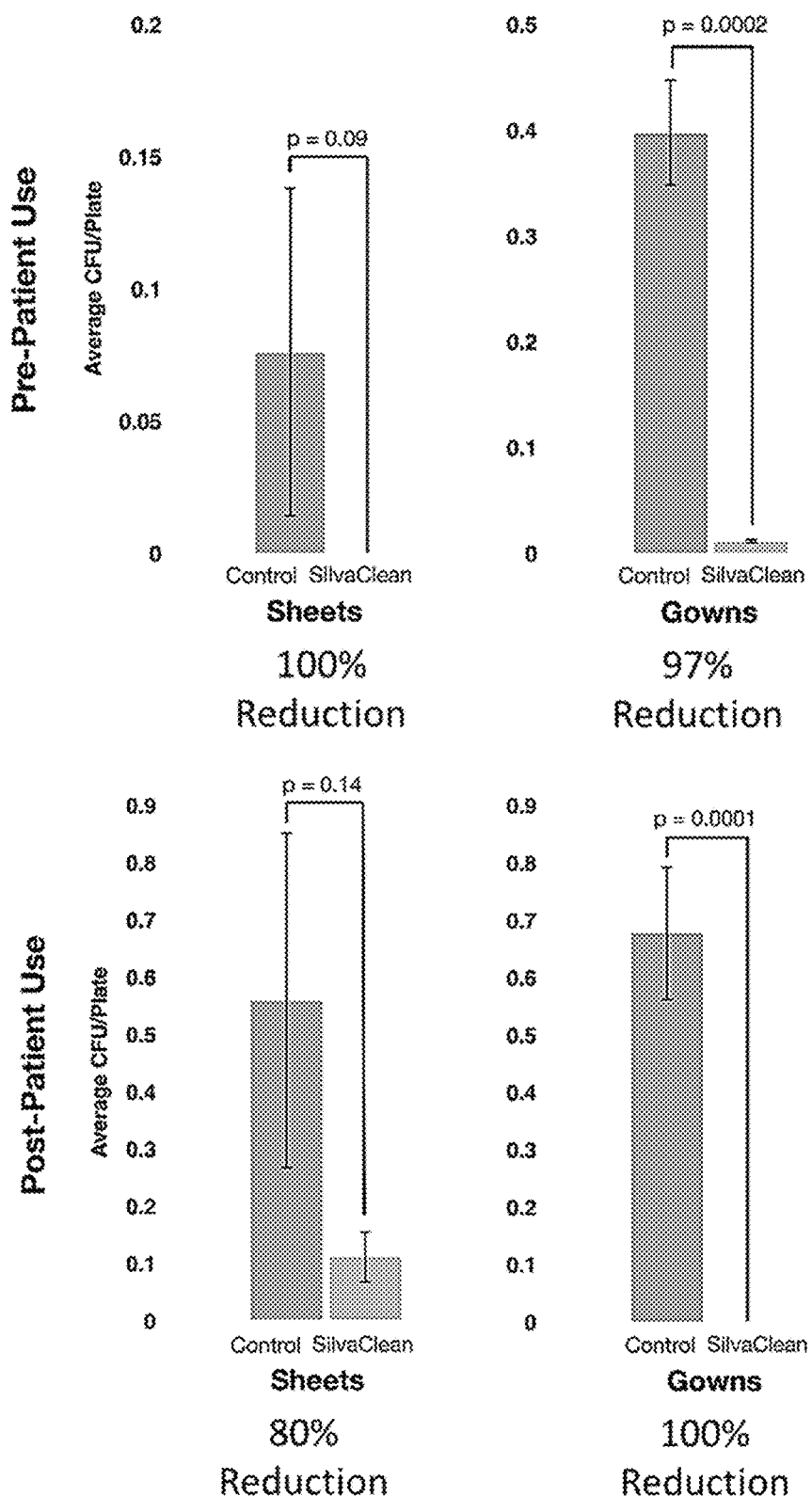
FIG. 10 shows the average CFU/plate for MRSA colonies before (control) and after silver application. Plates had a surface area of 28.27 cm$^2$.

While average colony counts of MRSA were much lower than colony counts on non-selective aerobic plates and *S. aureus* plates, the average number of MRSA colonies isolated per plate decreased after silver treatment (See, FIG. 10). Before patient use, there was a 97% reduction in the average number of MRSA colonies on gowns (average of 0.4+0.04 CFU/plate compared with 0.01+0.001 CFU/plate on silver treated gowns, p=0.0002) and a 100% reduction on sheets (average of 0.07+0.06 CFU/plate compared with no MRSA isolated on the silver treated sheets, p=0.09). After patient use, there was a 100% reduction in the average number of MRSA colonies on gowns (average of 0.7+0.1 CFU/plate compared with no MRSA isolated on the silver treated gowns, p=0.0001) and a 80% reduction on sheets (0.5+0.3 CFU/plate compared with 0.1+0.04 CFU/plate on the silver treated sheets, p=0.14).

The proportion of gowns with at least one colony of MRSA (See, Table 2) decreased from 29% (18/63) to 2% (1/47) after silver treatment (p=0.0002) in the pre-patient use group and from 26% (9/34) to 0% (0/49) after silver treatment (p=0.0001) in the post-patient use group. The proportion of sheets with at least one colony of MRSA decreased from 2% (2/32) to 0% (0/47) after silver treatment (p=0.16) in the pre-patient use group and from 21% (9/33) to 11% (7/64) in the post-patient use group (p=0.17).

In an unadjusted mixed-effects logistic model controlling only for hospital site clustering (See, Table 6), the presence of silver was associated with decreased isolation of MRSA (OR 0.3, 95% CI 0.1-0.9). In the best-fit multivariable mixed-effects logistic model for isolation of MRSA, only the presence or absence of silver was predictive of MRSA isolation.

TABLE 6

Unadjusted and Adjusted Mixed-Effects Logistic Models

| | MRSA Specific Media | | |
|---|---|---|---|
| | %(n) | Unadjusted (OR, 95% CI) | Adjusted (OR, 95% CI) |
| Ward Type | | | |
| Non-Monitored | 9% (27) | Ref | — |
| Monitored | 21% (19) | 1.6 (0.8-3.2) | — |
| Patient Exposure | | | |
| Pre-Use | 11% (21) | Ref | — |
| Post-Use | 13% (25) | 1.5 (0.8-2.9) | — |
| Textile Type | | | |
| Sheet | 10% (18) | Ref | — |
| Gown | 14% (28) | 1.2 (0.6-2.4) | — |
| Silver Treatment | | | |
| Absent | 22% (38) | Ref | Ref |
| Present | 4% (8) | 0.3 (0.1-0.9)* | 0.3 (0.1-0.9)* |

Abbreviations:
OR, Odds ratio;
CI, Confidence Interval;
*p < 0.05

Example 6: Silver Detection in Treated Textiles

A pass/fail method for detecting the presence of silver in a SILVACLEAN® treated textile was used to confirm the silver content of treated textiles. The detection kit includes two solutions, labeled Solution A and Solution B. Solution A and Solution B both include Cadion 2B (CAS No. 6708-61-8), which, in the presence of a surfactant at pH~9.6, forms a red-violet complex with silver. Solution B, which serves as a control solution, further includes sodium thiosulfate, which binds silver more strongly than Cadion B and prevents any color change.

Solution A was prepared by dissolving 1.56 g of Solution A Dry Components (See, Table 7) and 1.9 mL of Solution A Liquid Components (See, Table 8) in 50 mL $H_2O$.

TABLE 7

Solution A Dry Components

| Compound | Percent Range (w/w) |
|---|---|
| Potassium Borate | 50%-60% |
| Citric Acid | 1%-5% |
| Cadion 2B | <0.1% |
| CDTA, Disodium Magnesium Salt | 30%-40% |
| Sodium Citrate | 10%-20% |

TABLE 8

Solution A Liquid Components

| Compound | Percent Range (w/w) |
|---|---|
| 1-Methyl-2-pyrrolidinone | 70%-80% |
| TWEEN ® 20 Polyoxyethylene (20) Sorbitanmonolaurate | 20%-20% |

Solution B was prepared by transferring 25 mL of Solution A to a second vessel and adding 0.14 g sodium thiosulfate. Solution A and Solution B were stored in dropper bottles. The directions for use are as follows:
1. Ensure adequate lighting directly over the observation area.
2. Wearing Nitrile gloves and eye protection, remove both bottles (labeled Solution A and Solution B) from test kit.
3. Fold sample textile three times over itself (gather at least 8 layers) and place multi-layered section into the well-lit observation area.
4. Remove caps from both bottles and prepare to test.
5. Place 3 drops of Solution A onto a single spot, immediately place 3 drops of Solution B onto a spot located at least 1" to the right of the previous drops. Spots should not merge.
6. Replace caps and return bottles to package.
7. In 30 seconds, review the spots for color change.

After following the above directions, a difference in color indicates that that an efficacious level of silver is present in the tested textile.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of reducing a microbial load in an inventory of textiles comprising a plurality of pieces from a healthcare facility, the method comprising:
(a) receiving a first portion comprising a portion of the plurality of pieces of the inventory;
(b) measuring a quality of water for use in a treatment cycle for treating the inventory, wherein the measured water quality is used to make a determination in connection with an antimicrobial agent used in the treatment cycle, wherein the determination comprises determining whether a predetermined amount of the plurality of pieces of the inventory have achieved a predetermined antimicrobial efficacy and determining whether to proceed with the treatment cycle;
(c) initiating the treatment cycle, wherein the treatment cycle comprises a solution having a predetermined concentration of the antimicrobial agent, and wherein the antimicrobial agent comprises silver chloride or silver nitrate; and
(d) receiving a subsequent portion of the inventory and repeating step (c) in a subsequent treatment cycle for the subsequent portion, thereby reducing the antimicrobial load of the inventory.

2. The method of claim 1, wherein a single treatment cycle is insufficient to achieve a predetermined antimicrobial efficacy.

3. The method of claim 1, wherein the subsequent portion includes a plurality of pieces from the first portion.

4. The method of claim 1, further comprising repeating step (d) until a predetermined amount of the pieces of the inventory have achieved a predetermined antimicrobial efficacy, and wherein the predetermined amount of the pieces comprises at least 50% of the inventory.

5. The method of claim 4, wherein the predetermined antimicrobial efficacy is achieved when the textile is infused with at least approximately 1 mg of metallic ion per kg of textile.

6. The method of claim 1, wherein the solution comprises water treated by deionization or reverse osmosis.

7. The method of claim 1, further comprising, prior to or after any one or more of steps (a)-(d), detecting a presence of silver in a textile, the method comprising:
 (a) dispensing a first solution and a second solution onto separate areas of the textile, wherein the first solution comprises Cadion 2B, a buffer sufficient to maintain a pH in a range of from about 8 to about 10, and a surfactant, and the second solution comprises Cadion 2B, a buffer sufficient to maintain a pH in the range of from about 8 to about 10, a surfactant, and a complexing agent, wherein formation of a complex of the complexing agent and silver is more favorable than formation a complex of Cadion B and silver; and
 (b) comparing a color of the dispensed first solution and the dispensed second solution.

8. The method according to claim 7, wherein at least one of the first solution and the second solution further comprise a masking agent.

9. The method according to claim 8, wherein the masking agent is ethylenediaminetetraacetic acid (EDTA) or cyclohexanediaminetetraacetic acid (CDTA).

10. The method according to claim 7, wherein at least one of the first solution and the second solution further comprise a water-miscible organic solvent.

11. The method according to claim 10, wherein the water-miscible organic solvent is 1-methyl-2-pyrrolidinone.

12. The method according to claim 7, wherein the complexing agent is sodium thiosulfate.

13. The method according to claim 7, wherein the buffer comprises one or more of potassium tetraborate, citric acid, and sodium citrate.

14. The method of claim 1, wherein measuring a quality of water comprises measuring water hardness of water for use in the treatment cycle.

15. The method of claim 1, wherein measuring a quality of water comprises measuring at least one of calcium concentration or magnesium concentration of water for use in the treatment cycle.

16. The method of claim 1, wherein measuring a quality of water comprises measuring pH of water for use in the treatment cycle.

17. The method of claim 1, wherein measuring a quality of water comprises measuring total dissolved solids (TDS) concentration of water for use in the treatment cycle.

18. The method of claim 1, wherein the method further comprises generating a Relative Water Quality (RWQ) number, wherein the RWQ number is based on at least the measured quality of water for use in the treatment cycle.

19. The method of claim 1, wherein the determination further comprises determining whether to initiate the treatment cycle.

20. The method of claim 1, wherein the determination further comprises determining whether to treat the plurality of pieces with the antimicrobial agent in the treatment cycle.

21. The method of claim 1, wherein the determination further comprises determining an updated concentration of the antimicrobial agent in the treatment cycle.

22. The method of claim 1, wherein the determination further comprises:
 based on the measured quality of water for use in a treatment cycle, determining that the predetermined antimicrobial efficacy of the plurality of pieces of the inventory has not been achieved; and
 based on the determining, transmitting a signal.

23. The method of claim 1, wherein the antimicrobial agent further comprises one or more of the following: silver acetate, silver carbonate, silver oxide, and silver sulfate.

\* \* \* \* \*